United States Patent [19]

Ochiai et al.

[11] Patent Number: 5,532,342
[45] Date of Patent: Jul. 2, 1996

[54] AZO METAL CHELATE COMPOUND

[75] Inventors: Tameichi Ochiai, Sagamihara; Yutaka Kurose, Kawasaki; Takumi Nagao, Yokohama; Takako Tsukahara, Sagamihara; Satoru Imamura, Machida, all of Japan

[73] Assignee: Mitsubishi Chemical Corporation, Tokyo, Japan

[21] Appl. No.: 422,948

[22] Filed: Apr. 17, 1995

Related U.S. Application Data

[62] Division of Ser. No. 70,664, Jun. 2, 1993, Pat. No. 5,447,823.

[30] Foreign Application Priority Data

Jun. 2, 1992 [JP] Japan ................... 4-141812
Oct. 7, 1992 [JP] Japan ................... 4-268857

[51] Int. Cl.⁶ ............... C09B 29/042; C09B 29/045; C09B 29/09; B41M 5/26
[52] U.S. Cl. ............. 534/693; 534/703; 534/705; 534/706; 534/707; 534/752; 534/768; 534/770; 534/781; 534/782; 534/785; 534/795; 430/270.1; 430/495.1; 430/945
[58] Field of Search .................. 534/782, 673, 534/703, 705, 706, 707, 752, 768, 770, 781, 782, 785, 795

[56] References Cited

U.S. PATENT DOCUMENTS 4,686,143  8/1987  Yoshikawa et al. ............ 428/211.1
5,298,608  3/1994  Murayama et al. ............ 534/693

FOREIGN PATENT DOCUMENTS 2716033  10/1978  Germany ............ 534/782
2805304  8/1979  Germany ............ 534/782
2026520  2/1980  United Kingdom ............ 534/782
2026519  2/1980  United Kingdom ............ 534/782

OTHER PUBLICATIONS

Yoshikawa et al II, Chemical Abstracts, vol. 107, #49694w (1987).

Primary Examiner—Floyd D. Higel
Attorney, Agent, or Firm—Oblon, Spivak, McClelland, Maier & Neustadt

[57] ABSTRACT

An azo metal chelate compound of an azo compound of the formula (I) with a metal:

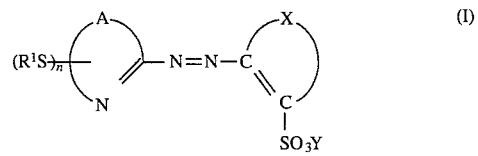

wherein A is a residue forming a heterocyclic ring together with the carbon atom and the nitrogen atom to which it is bonded, X is a residue forming an aromatic group together with the two carbon atoms to which it is bonded, $R^1$ is an alkyl group which may be substituted, an aryl group which may be substituted, an alkenyl group which may be substituted, or a cycloalkyl group which may be substituted, Y is a hydrogen atom or a cation, and n is an integer of from 1 to 3.

4 Claims, 12 Drawing Sheets

AZO METAL CHELATE COMPOUND

This is a division of application Ser. No. 08/070,664, filed on Jun. 2, 1993, now U.S. Pat. No. 5,447,823.

The present invention relates to a novel azo metal chelate compound of an azo compound with a metal, an intermediate thereof and an optical recording medium using such a compound.

Optical recording employing a laser has found remarkable developments in recent years, as it makes the storage of high density information recording and its reproduction possible.

As an example of an optical recording medium, an optical disc may be mentioned. In general, an optical disc is designed so that high density information recording is conducted by irradiating a laser beam focused to about 1 µm to a thin recording layer provided on a disc-shape substrate. The recording is conducted in such a manner that upon absorption of the irradiated laser beam energy, such a portion of the recording layer undergoes a thermal deformation such as decomposition, evaporation or dissolution. Further, the reproduction of the recorded information is conducted by reading the difference in reflectance between the portion where such a deformation was formed by the laser beam and a portion where no such deformation was formed.

Accordingly, the optical recording medium is required to efficiently absorb the laser beam energy, and a laser-absorbing dye is employed.

Various constructions have been known for optical recording media of this type. For example, Japanese Unexamined Patent Publication No. 97033/1980 discloses a medium having a single layer of a phthalocyanine type dye provided on a substrate. However, the phthalocyanine type dye has a problem that the sensitivity is low, and the decomposition point is high and vapor deposition is difficult. Further, it has an additional problem such that the solubility in an organic solvent is very poor, whereby it can not be used for coating in the form of a coating solution.

On the other hand, Japanese Unexamined Patent Publications No. 112790/1983, No. 114989/1983, No. 85791/1984 and No. 83236/1985 disclose media having cyanine-type dyes as the respective recording layers. Such dyes have high solubility and thus have a merit that they can be applied by coating in the form of coating solutions. However, they also have a problem that they are inferior in the light resistance. In this connection, Japanese Unexamined Patent Publication No. 55795/1984 proposes to improve the light resistance by an addition of a quencher to such a cyanine type dye. However, such a proposal is still at an inadequate level.

In connection with such problems, Japanese Unexamined Patent Publication No. 30090/1987 discloses a recording medium wherein a complex of a monoazo compound with a metal, is employed, as a recording medium having the solubility in an organic solvent and the light resistance improved. However, such a compound is inferior in the sensitivity with the light sensitive wavelength being short, and further it is inferior in the storage stability under a high temperature high humidity condition, whereby it has problems as an optical recording medium.

It is an object of the present invention to provide, as a recording dye and an optical recording medium using it, an azo metal chelate compound of an azo compound with a metal excellent in the sensitivity, the storage stability and the weather resistance and suitable for spin coating, and an optical recording medium using such a compound, which solve the above problems.

The present invention provides an azo metal chelate compound of an azo compound of the formula (I) with a metal:

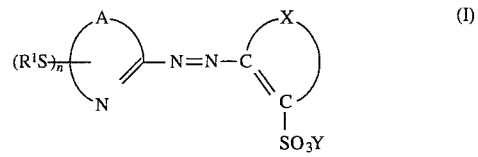

wherein A is a residue forming a heterocyclic ring together with the carbon atom and the nitrogen atom to which it is bonded, X is a residue forming an aromatic group together with the two carbon atoms to which it is bonded, $R^1$ is an alkyl group which may be substituted, an aryl group which may be substituted, an alkenyl group which may be substituted, or a cycloalkyl group which may be substituted, Y is a hydrogen atom or a cation, and n is an integer of front 1 to 3.

The present invention also provides an optical recording medium having a recording layer provided on a substrate so that information can be written in and/or read out by a laser, wherein the recording layer contains the above azo metal chelate compound.

Further, the present invention provides an aminobenzothiazole compound of the following formula (1):

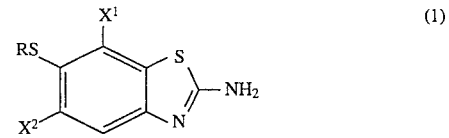

wherein R is $C_nH_mF_{2n-m+1}$ wherein n is 2 or 3, and m is an integer of from 0 to 2n, and each of $X^1$ and $X^2$ which are independent of each other, is a hydrogen atom, a chlorine atom or a methyl group.

Furthermore, the present invention provides an aniline compound of the formula (2):

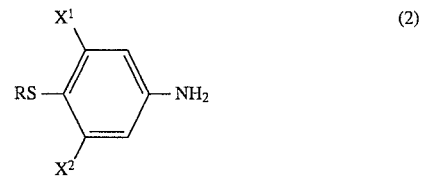

wherein R is $C_nH_mF_{2n-m+1}$ wherein n is 2 or 3, and m is an integer of from 0 to 2n, and each of $X^1$ and $X^2$ which are independent of each other, is a hydrogen atom, a chlorine atom or a methyl group.

The aminothiazole compound of the formula (1) can be prepared by a process which comprises reacting a thiocyanate to the aniline compound of the formula (2). The aniline compound of the formula (2) can be prepared by a process which comprises reacting a halogenated alkyl compound of the formula $C_nH_mF_{2n-m+1}Y$ wherein n and m are as defined above, and Y is a bromine atom or an iodine atom, to an aminothiophenyl compound of the following formula (3):

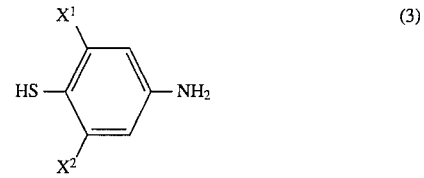

wherein $X^1$ and $X^2$ are as defined above.

Now, the present invention will be described in detail.

Figure 1:
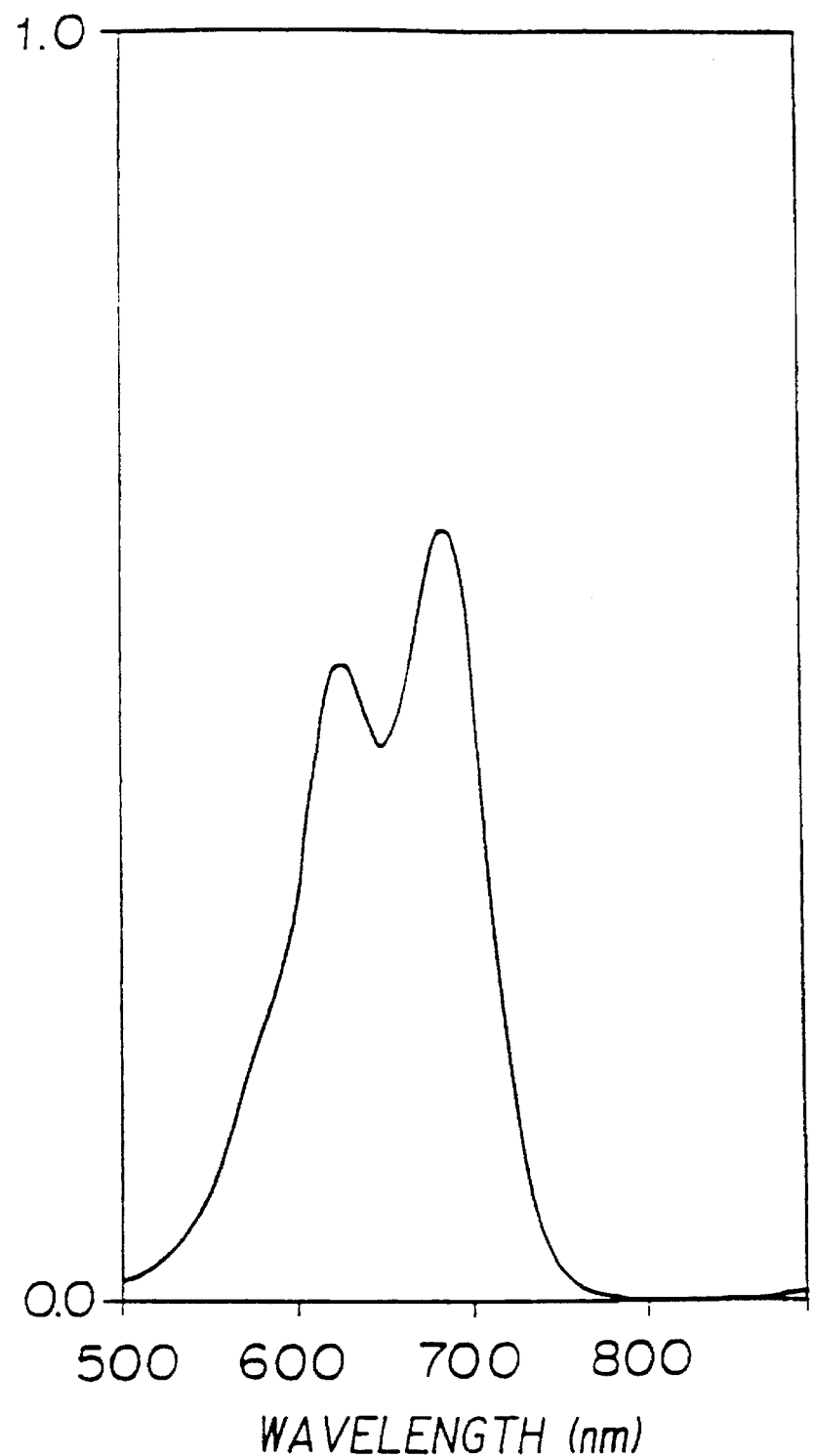
FIG. 1 is a graph showing a visible range absorption spectrum of the nickel chelate compound of Example 1 as measured in a chloroform solution.

A preferred azo compound in the present invention is a compound of the formula (II):

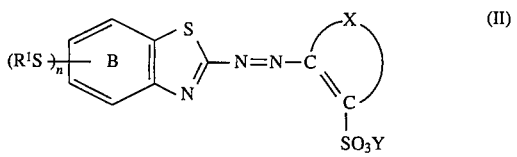

wherein ring B may have a substituent other than $-SR^1$, X is a residue forming an aromatic group together with the two carbon atoms to which it is bonded, $R^1$ is an alkyl group which may be substituted, an aryl group which may be substituted, an alkenyl group which may be substituted, or a cycloalkyl group which may be substituted, Y is a hydrogen atom or a cation, and n is an integer of from 1 to 3.

A more preferred azo compound is a compound of the formula (III):

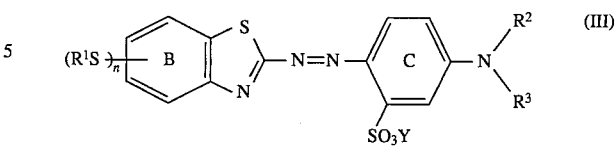

wherein ring B may have a substituent other than $-SR^1$, ring C may have a substituent other than $-SO_3Y$, $R^1$ is an alkyl group which may be substituted, an aryl group which may be substituted, an alkenyl group which may be substituted, or a cycloalkyl group which may be substituted, each of $R^2$ and $R^3$ which are independent of each other, is a hydrogen atom, an alkyl group which may be substituted, an aryl group which may be substituted, an alkenyl group which may be substituted, or a cycloalkyl group which may be substituted, Y is a hydrogen atom or a cation, and n is an integer of from 1 to 3.

A still more preferred azo compound is a compound of the formula (IV):

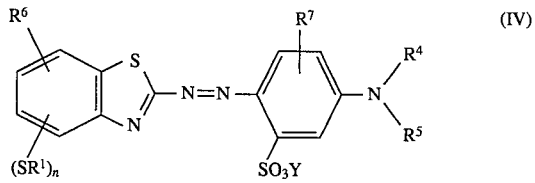

wherein $R^1$ is an alkyl group which may be substituted, an aryl group which may be substituted, an alkenyl group which may be substituted, or a cycloalkyl group which may be substituted, each of $R^4$ and $R^5$ which are independent of each other, is a $C_{1-6}$ alkyl group or a $C_{2-7}$ alkoxyalkyl group, each of $R^6$ and $R^7$ which are independent of each other, is a hydrogen atom, a $C_{1-6}$ alkyl group, a $C_{1-6}$ alkoxy group or a cation, and n is an integer of from 1 to 3.

A particularly preferred azo compound is a compound of the formula (V):

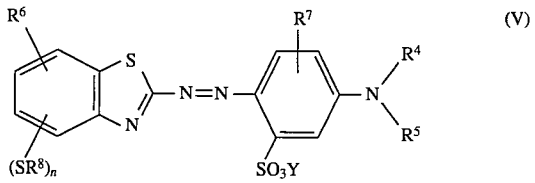

wherein each of $R^4$ and $R^5$ which are independent of each other, is a $C_{1-6}$ alkyl group or a $C_{2-7}$ alkoxyalkyl group, each of $R^6$ and $R^7$ which are independent of each other, is a hydrogen atom, a $C_{1-6}$ alkyl group, a $C_{1-6}$ alkoxy group or a halogen atom, $R^8$ is a $C_{1-6}$ alkyl group, of which at least one hydrogen atom is substituted by a fluorine atom, Y is a hydrogen atom or a cation, and n is an integer of from 1 to 3.

A in the formula (I) is not particularly limited so long as it forms a heterocyclic ring together with the carbon atom and the nitrogen atom to which it is bonded. For example,

in the formula (I) may be the following:

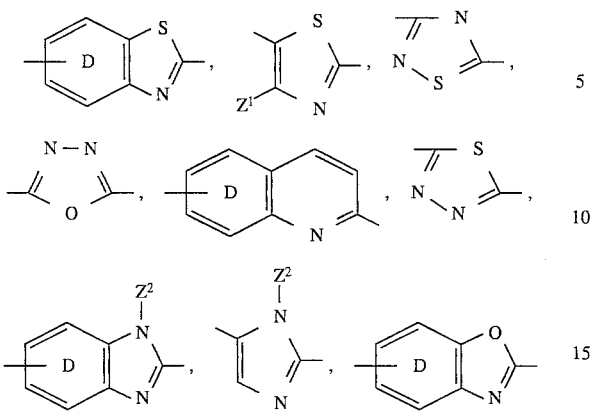

In the above formulas, ring D may have a substituent, and the substituent may, for example, be an alkyl group, an alkoxy group, a halogen atom, an alkylsulfonyl group, an alkylcarbonyl group, a formyl group, a nitro group, a trifluoromethyl group, a trifluoromethoxy group, a cyano group or an alkylthio group, $Z^1$ may, for example, be a hydrogen atom, an alkyl group, a halogen atom or an aryl group, and $Z^2$ may, for example, be a hydrogen atom or an alkyl group.

X is a group which forms an aromatic ring such as a benzene ring or a naphthalene ring together with the two carbon atoms to which it is bonded.

In the formula (II), the substituent on ring B other than —$SR^1$ may, for example, be an alkyl group, an alkoxy group, a halogen atom, a nitro group, a cyano group, an alkylsulfonyl group, an alkylcarbonyl group, a trifluoromethyl group, a trifluoromethoxy group, an alkylthio group or a formyl group.

In the formula (III), the substituent on ring C other than —$SO_3Y$ may, for example, be an alkyl group, an alkoxy group or a halogen atom, and each of $R^2$ and $R^3$ may, for example, be a hydrogen atom, or a $C_{1-20}$ alkyl, aryl, alkenyl or cycloalkyl group, which may be substituted. The substituent on the alkyl, aryl, alkenyl or cycloalkyl group for each of $R^2$ and $R^3$ may, for example, be an alkoxy group, an alkoxyalkoxy group, an alkoxyalkoxyalkoxy group, an allyloxy group, an aryl group, an aryloxy group, a cyano group, a nitro group, a hydroxyl group, a tetrahydrofuryl group, an alkylsulfonylamino group or a halogen atom. Further, the substituent on the aryl or cycloalkyl group may be an alkyl group or a vinyl group.

In the present invention, specific examples of the azo compound which forms a chelate compound together with a metal, include the following compounds, which may be used alone or in combination as a mixture of two or more of them.

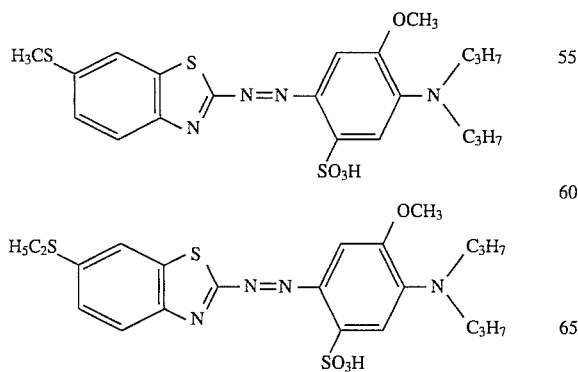

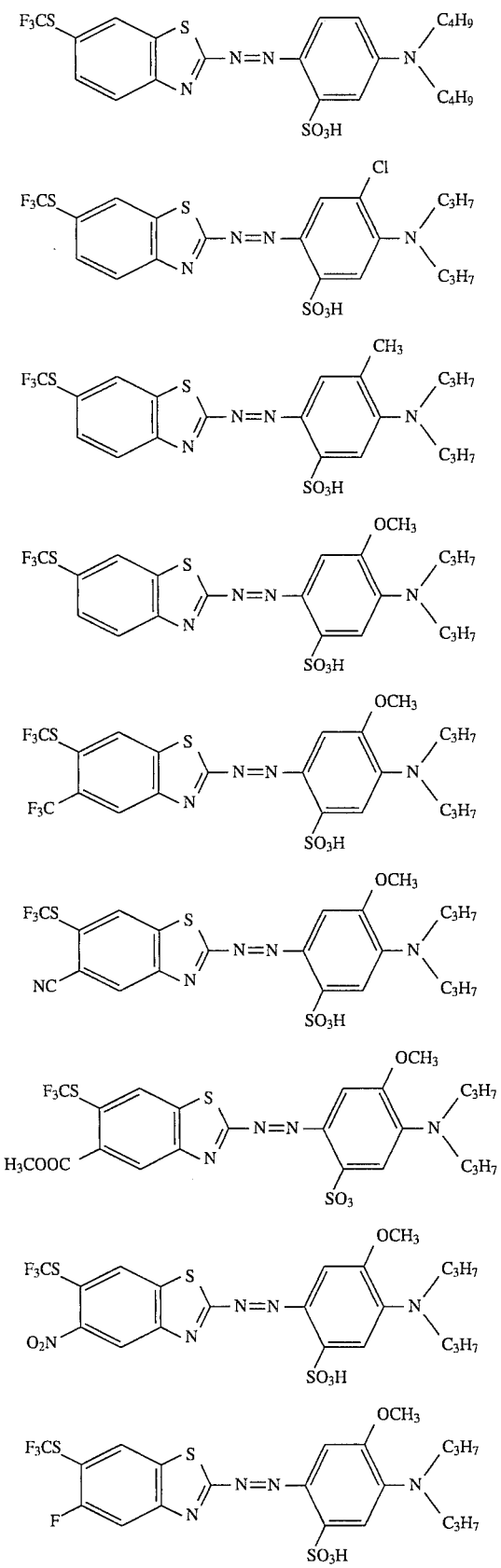

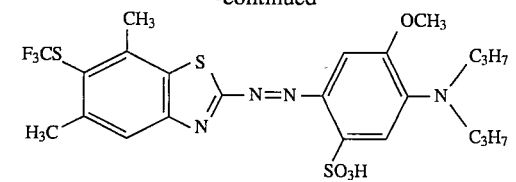
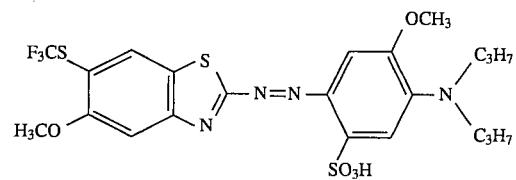
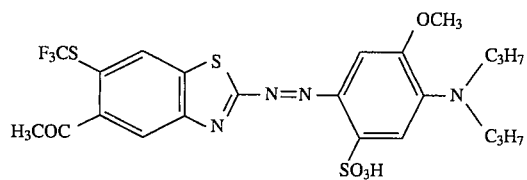
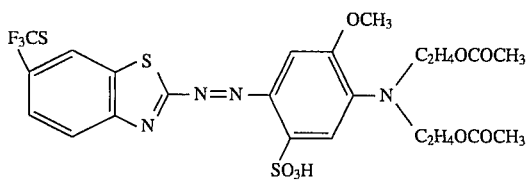
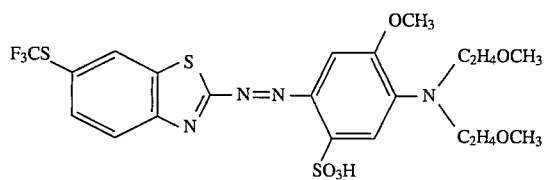
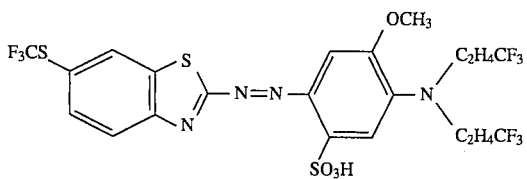
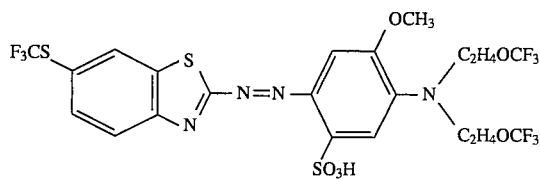
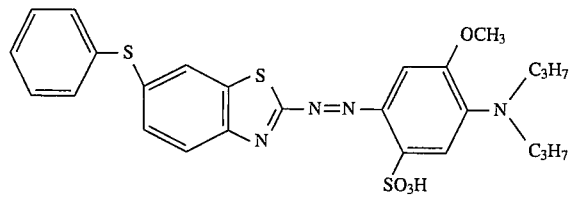
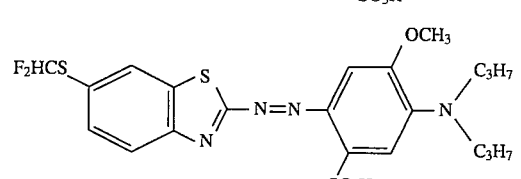
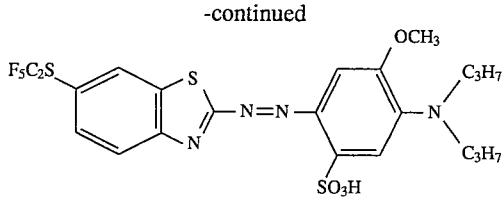
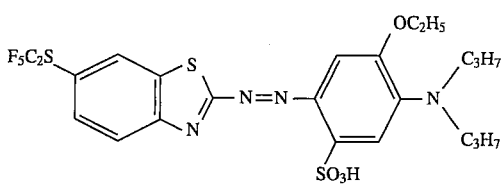
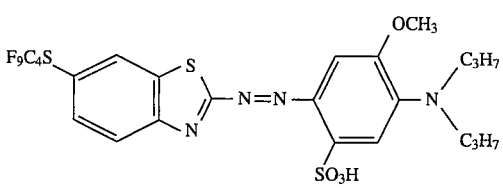
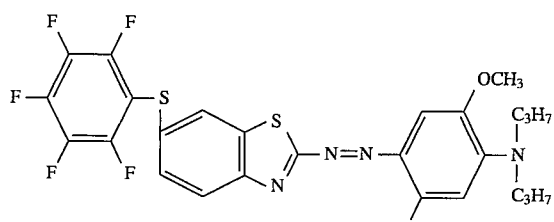
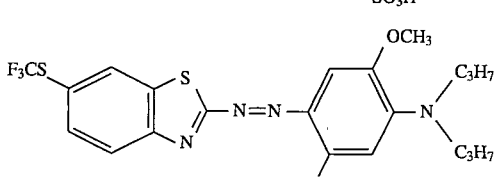
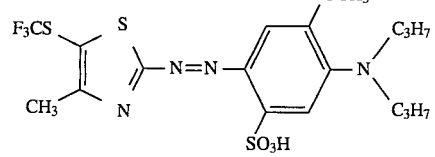
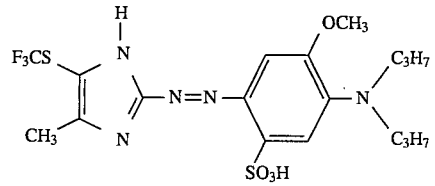
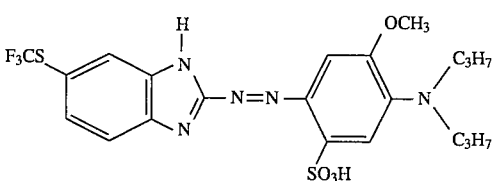
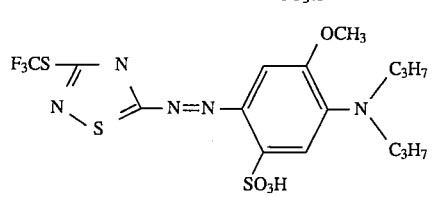

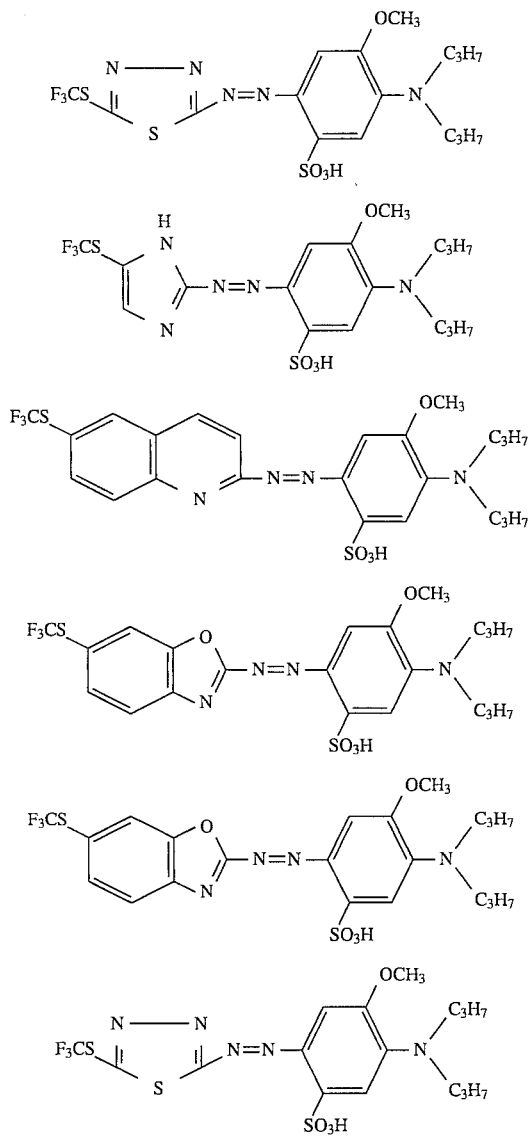

In the present invention, the metal which forms a chelate compound together with the azo compound, is not particularly limited so long as it is a metal capable of forming a chelate compound together with the above described azo compound. However, a transition element such as Ni, Co, Fe, Ru, Rh, Pd, Os, Ir or Pt is preferred. Particularly preferred is Ni or Co.

The azo metal chelate compound of the present invention may be prepared, for example, in accordance with the following reaction scheme:

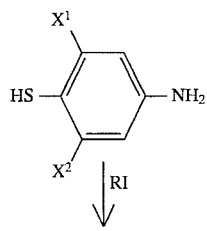

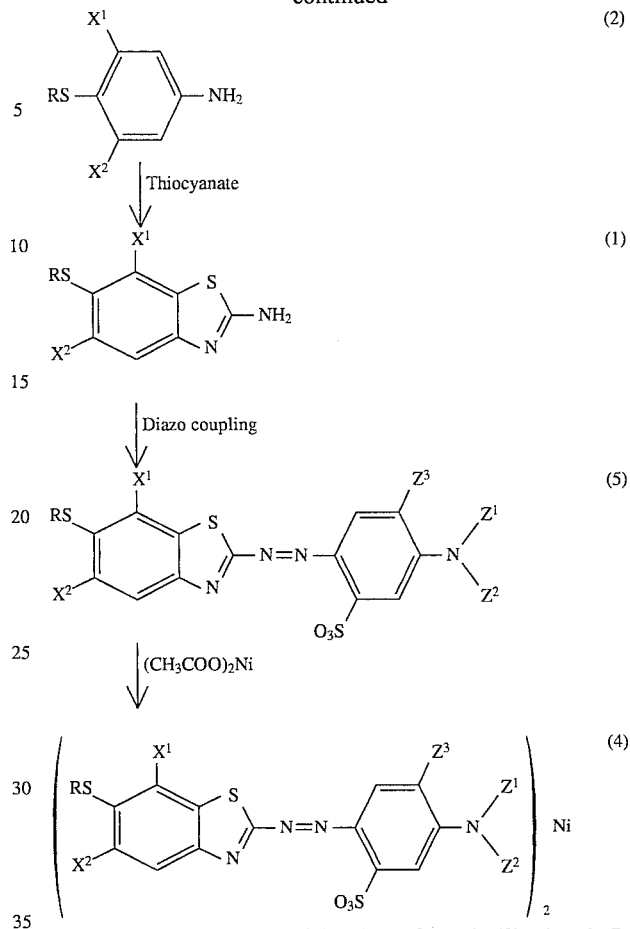

An aniline compound of the above formula (2) wherein R is $C_nH_mF_{2n-m+1}$ wherein n is 2 or 3, and m is an integer of from 0 to 2n, and each of $X^1$ and $X^2$ which are independent of each other, is a hydrogen atom, a chlorine atom or a methyl group, can be obtained by reacting a halogenated alkyl compound of the formula $C_nH_mF_{2n-m+1}Y$ wherein n and m are as defined above, and Y is a bromine atom or an iodine atom, to an aminothiophenol compound of the above formula (3) wherein $X^1$ and $X^2$ are as defined above.

The above reaction is preferably conducted in a solvent. The solvent is not particularly limited, but a polar solvent is preferably employed. For example, dimethylformamide, tetrahydrofuran or an alcohol may be employed. In such a solvent, the aminothiophenol compound of the above formula (3) and the halogenated alkyl compound of the formula $C_nH_mF_{2n-m+1}$ Y wherein n, m and Y are as defined above, are reacted in the presence of a suitable alkali such as potassium carbonate, sodium carbonate, sodium hydroxide, potassium hydroxide or triethylamine. The reaction can be conducted at a temperature of from −10° C. to 40° C., preferably at a temperature of not higher than 20° C., particularly preferably at a temperature of from 5° to 10° C. Further, a catalyst such as a crown ether or a phase transfer catalyst may be added to the reaction system. A method is particularly preferred in which prior to the addition of the halogenated alkyl compound, sodium hydride, sodium metal, sodium alcoholate or sodium amide is preliminarily reacted to the aminothiophenol compound to form a thioalcoholate, and then the halogenated alkyl compound is reacted thereto, since the yield is thereby high. From the viewpoint of the reactivity, it is particularly preferred to employ sodium hydride. Further, it is possible to employ an alkali compound such as potassium hydroxide or sodium hydroxide instead of sodium hydride or sodium metal.

An aminobenzothiazole compound of the above formula (1) can be prepared by using the aniline compound of the above formula (2) as the starting material.

For its preparation, various methods including those disclosed in ORGANIC REACTIONS, Vol 3, Chapter 6, John Willey and Sons, Inc. (1946) New York or in Organic Synthesis Collective Volume 2, p76–78, may be employed. However, a method of reacting bromine in an acetic acid solvent in the presence of a thiocyanate is particularly preferred, since it is simple and gives good yield. The thiocyanate may, for example, be a salt of K, Na, Li or $NH_4$.

Now, the diazo coupling reaction and subsequent steps will be described.

An amino compound of the formula (VI):

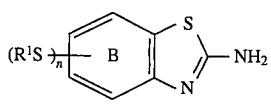

wherein ring B, $R^1$ and n are as defined above, is diazotized by a conventional method, followed by coupling with a substituted aniline sulfonic acid derivative of the following formula (VII):

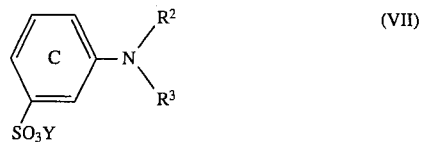

wherein ring C, $R^2$, $R^3$ and Y are as defined above, to obtain an azo compound of the above-mentioned formula (III). Then, the azo compound and the metal salt are reacted in water and/or an organic solvent, such as dioxane, tetrahydrofuran, acetone, ethanol or methanol, to obtain an azo metal chelate compound of the present invention.

As the anion of the metal salt to be used for the preparation of the metal chelate compound, a monovalent or bivalent anion such as $SCN^-$, $SbF_6^-$, $Cl^-$, $Br^-$, $F^-$, $ClO_4^-$, $BF_4^-$, $PF_6^-$, $CH_3COO^-$, $TiF_6^{2-}$, $SiF_6^{2-}$, $Ph-SO_3^-$, $CH_3-Ph-SO_3^-$ or $B^--(Ph)_4$, may be mentioned. Particularly preferred is $CH_3COO^-$. In the above formulas, Ph represents a benzene ring.

The optical recording medium of the present invention consists essentially of a substrate and a recording layer containing the above metal chelate compound of an azo compound. However, if necessary, an undercoating layer may be provided on the substrate. Further, as a preferred layer structure, a metal reflective layer of e.g. gold or aluminum, and a protective layer may be formed on the recording layer to obtain a medium having a high reflectance and to obtain a writable CD medium.

The substrate in the present invention is preferably transparent to the laser beam to be used, and it may be a usual support for the recording material such as glass or plastic. However, plastics are preferably used from various reasons. Such plastics include, for example, acryl resin, methacryl resin, vinylacetate resin, vinyl chloride resin, nitrocellulose, polyethylene resin, polypropylene resin, polycarbonate resin, polyimide resin, epoxy resin, and polysulfone resin. Among them, a polycarbonate resin substrate of injection molding type is particularly preferred, from the viewpoint of the productivity, cost and moisture resistance.

The recording layer containing the chelate compound of the azo compound with a metal in the optical recording medium of the present invention, preferably has a thickness of from 100 Å to 5 μm, more preferably from 700 Å to 3 μm. With respect to the layer-forming method, a layer may be formed by a conventional thin layer-forming method such as a vacuum deposition method, a sputtering method, a doctor blade method, a casting method, a spinning method or a dipping method. The spinning method is preferred from the viewpoint of the mass productivity and the cost.

Further, a binder may be used as the case requires. As the binder, a conventional binder such as polyvinyl alcohol, polyvinylpyrrolidone, ketone resin, nitrocellulose, cellulose acetate, polyvinylbutyral, or polycarbonate, may be employed. In the case of layer-forming by a spinning method, the rotational speed is preferably from 500 to 5,000 rpm. After the spin coating, treatment such as heating or application of a solvent vapor may be conducted as the case requires.

For improvement of the stability and the light resistance of the recording layer, a transition metal chelate compound (such as acetylacetonate chelate, bisphenyldithiol, salithylaldehydeoxime or a bisdithio-α-diketone) may be incorporated as a singlet state oxygen quencher. Further, an additional dye may be used in combination, as the case requires. Such an additional dye may be a homologous dye, or a dye in a different category, such as a triallylmethane type dye, an azo dye, a cyanine type dye, a squallilium type dye or a nickel-indoaniline type dye.

In a case of forming a recording layer by a doctor blade method, a casting method, a spinning method or a dipping method, particularly by a coating method such as a spin coating method, as the coating solvent, a solvent having a boiling pint of from 120° to 160° C., such as tetrafluoropropanol, octafluoropentanol, tetrachloroethane, bromoform, dibromoethane, diacetone alcohol, ethylcellosolve, xylene, 3-hydro-3-methyl-2-butanone, chlorobenzene, cyclohexanone, or methyl lactate, may suitable be used.

Among them, a ketone alcohol type solvent such as diacetone alcohol, or 3-hydroxy-3-methyl-2-butanone; a cellosolve type solvent such as methylcellosolve, or ethylcellosolve; a perfluoroalkyl alcohol type solvent such as tetrafluoropropanol, or octafluoropentanol; or a hydroxyester type solvent such as methyl lactate, or methyl isobutyrate, may be mentioned as a solvent particularly useful for an injection type polycarbonate resin substrate which is excellent in the productivity, cost and moisture resistance, without damaging the substrate.

The recording layer of the optical recording medium of the present invention may be provided on each side of the substrate or may be provided on one side only.

Recording on the recording medium thus obtained, is conducted by irradiating a laser beam, preferably a semiconductor laser beam, focused to a size of 1 μm on the recording layer provided on each side or one side of the substrate. At the portion irradiated with the laser beam, a thermal deformation of the recording layer, such as decomposition, evaporation or melting, takes place due to absorption of the laser energy.

Reproduction of the recorded information can be conducted by reading by a laser beam the difference in reflectance between the portion where a thermal deformation has taken place and the portion where no such deformation has taken place.

As the laser beam to be used for recording and reproduction of the optical recording medium of the present invention, a $N_2$, He-Cd, Ar, He-Ne, ruby, semiconductor or dye laser may be mentioned. However, from the viewpoint of the light weight, easy handling and compactness, a semiconductor laser is preferably employed.

Now, the present invention will be described in further detail with reference to Examples. However, it should be understood that the present invention is by no means restricted by such specific Examples.

PREPARATION EXAMPLE 1

Under a nitrogen stream, 1.92 g of 60% sodium hydride was dispersed in 40 ml of dimethylformamide (DMF), and a solution having 5.0 g (0.04 mol) of p-aminothiophenol of the following structural formula (6) dissolved in 60 ml of DMF, was dropwise added thereto at 10° C. over a period of about 20 minutes.

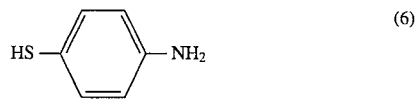
(6)

Then, the reaction solution was cooled to 5° C. Then, a solution having 25 g (2.5 mol) of $CF_3CF_2I$ (boiling point: 11°–12° C.) dissolved in 60 ml of DMF, was dropwise added thereto over a period of 15 minutes. The mixture was stirred for 5 hours at a temperature of from 5 to 10° C. and then left to stand overnight. The mixture was then put into 400 ml of water.

A precipitated oily substance was extracted with 200 ml of chloroform, washed with water and then dried over anhydrous sodium sulfate. Chloroform was distilled off under reduced pressure, and 15.02 g of an oily substance thereby obtained was distilled under reduced pressure, whereby after separating 2.38 g of an initial fraction having a boiling point of from 35 to 93° C. at from 5 to 6 mmHg, 7.51 g (yield: 77.3%) of p-aminophenylpentafluoroethylsulfide of the following structural formula (7) having a boiling point of from 93° to 98° C. (at from 5 to 6 mmHg) was obtained. The IR spectrum of the obtained compound is shown in FIG. 1.

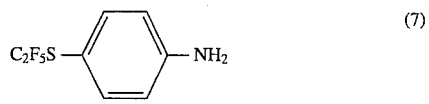
(7)

PREPARATION EXAMPLE 2

Under a nitrogen stream, 1.92 g of 60% sodium hydride was dispersed in 40 ml of DMF, and a solution having 5.0 g (0.04 mol) of p-aminothiophenol dissolved in 60 ml of DMF, was dropwise added thereto at 10° C. over a period of about 20 minutes.

Then, the reaction solution was cooled to 5° C. Then, a solution having 17.75 g (1.5 mol) of $CF_3CF_2I$ (boiling point: 39° C.) dissolved in 60 ml of DMF, was dropwise added thereto over a period of about 15 minutes. The mixture was stirred for 5 hours at a temperature of from 5° to 10° C. and then left to stand overnight. The mixture was then poured into 400 ml of water.

Figure 2:
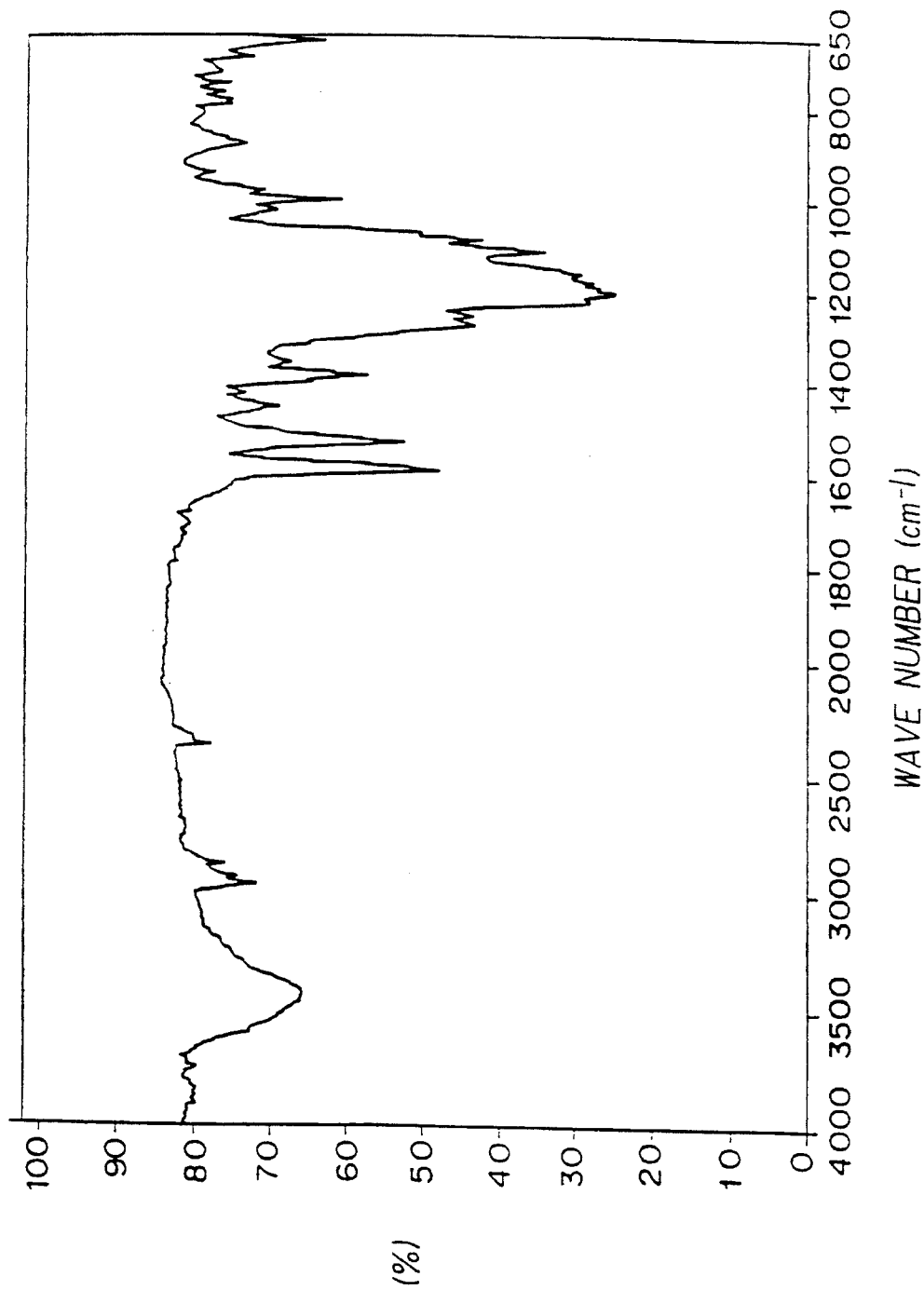
FIG. 2 is a graph showing an infrared absorption spectrum of the nickel chelate compound of Example 1.

A precipitated oily substance was extracted with 200 ml of chloroform, washed with water and then dried over anhydrous sodium sulfate. Chloroform was distilled off under reduced pressure, and an oily substance thereby obtained was distilled under reduced pressure, whereby after separating 4.50 g of an initial fraction having a boiling point of from 35° to 95° C. at from 3 to 4 mmHg, 6.25 g (yield: 53.3%) of p-aminophenylheptafluoro-n-propylsulfide of the following structural formula (8) having a boiling point of from 95° to 98° C. (3 to 4 mmHg) was obtained. The IR spectrum of the obtained compound is shown in FIG. 2.

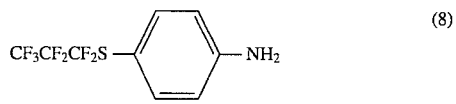
(8)

PREPARATION EXAMPLE 3

Figure 3:
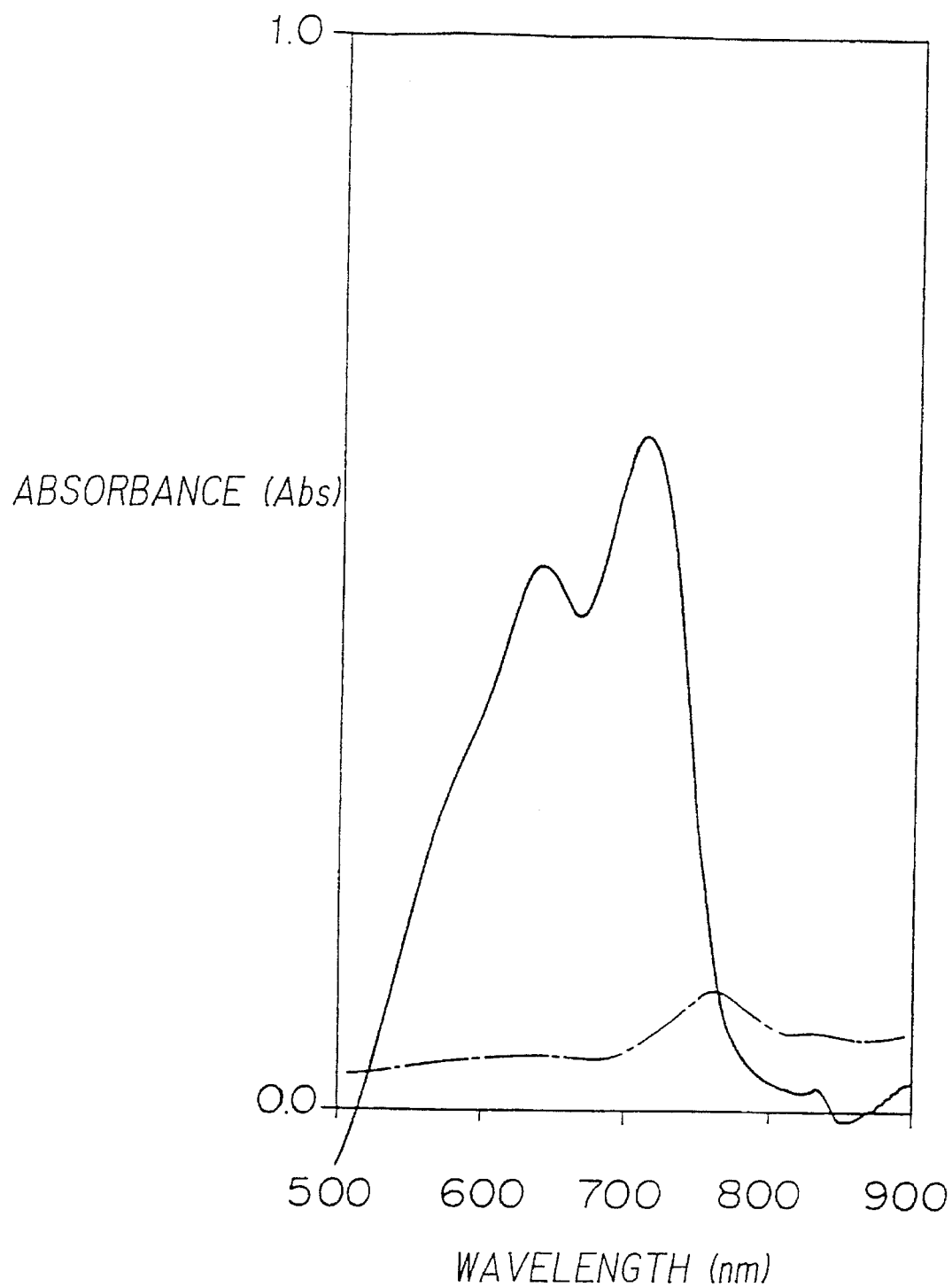
FIG. 3 is a graph showing a visible range absorption spectrum of the thin coating film of the nickel chelate compound of Example 1.

A solution containing 6.0 g (37.5 mmol) of bromine in 15 ml of acetic acid, was slowly dropwise added at 10° C. to a solution containing 7.30 g (30 mmol) of p-aminophenylpentafluoroethylsulfide and 9.13 g (120 mmol) of ammonium thiocyanate in 75 ml of acetic acid and 3.8 ml of water. The mixture was stirred for 3 hours and then left to stand overnight. The mixture was further heated and stirred for three hours at a temperature of from 70° to 80° C. Insoluble matters were removed by filtration while the mixture was still hot. The filtrate was poured into 300 ml of hot water, and the mixture was again subjected to hot filtration to remove insoluble matters. Under cooling with ice, 57 g of sodium carbonate was added to the filtrate, and the mixture was adjusted to pH5. Precipitated crystals were collected by filtration, then washed with water and dried to obtain 6.94 g (yield: 77.1%) of 2-amino-6-(pentafluoroethylthio)benzothiazole of the following structural formula (9) as slightly yellow crystals. MASS spectrum $M^+=300$, and the melting point was from 111° to 113° C. The IR spectrum is shown in FIG. 3.

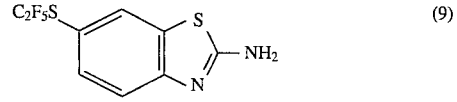
(9)

PREPARATION EXAMPLE 4

Figure 4:
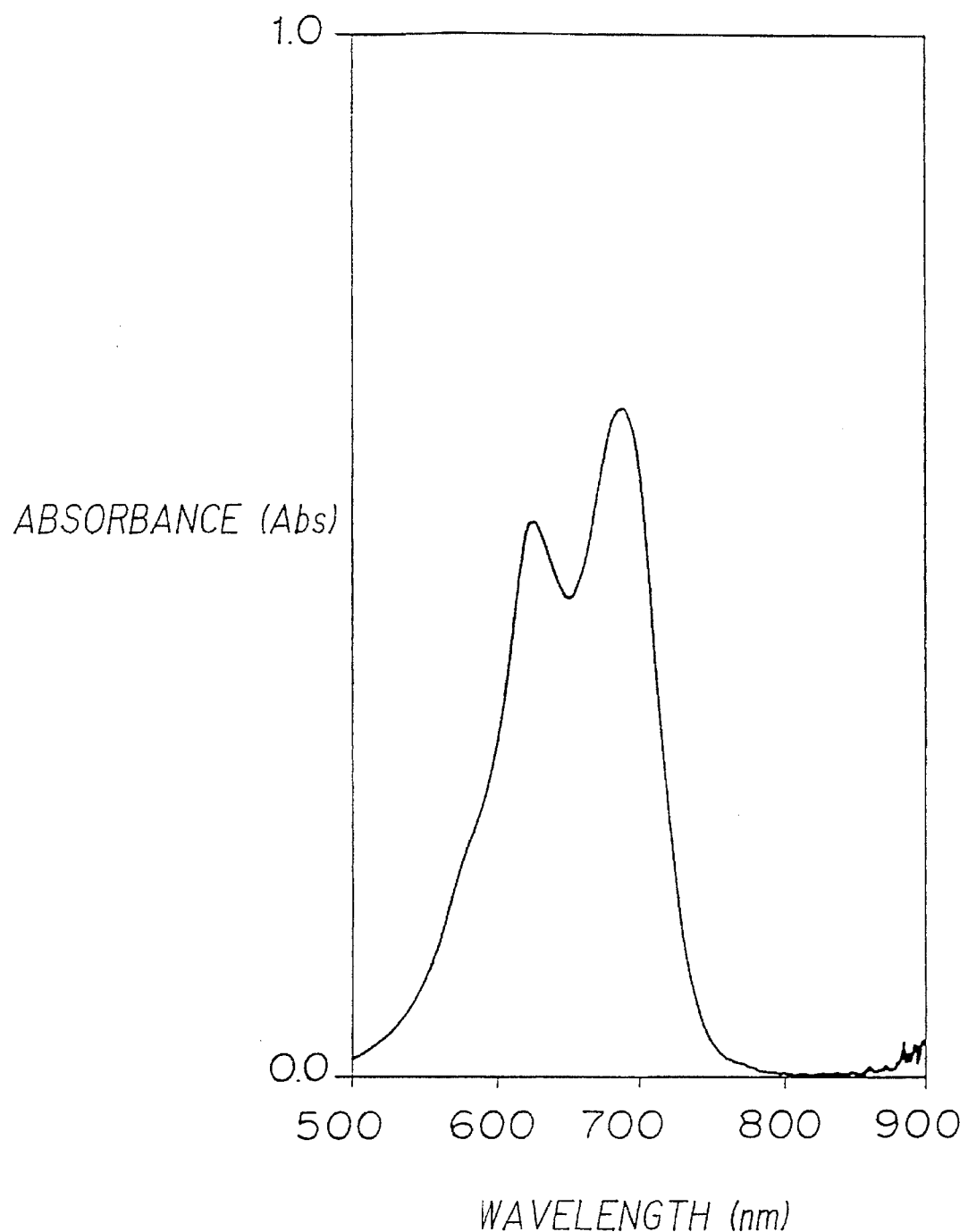
FIG. 4 is a graph showing a visible range absorption spectrum of the nickel chelate compound of Example 2 as measured in a chloroform solution.

A solution containing 4.0 g (25 mmol) of bromine in 10 ml of acetic acid, was slowly dropwise added at 10° C. to a solution containing 5.86 g (20 mmol) of p-aminophenylheptafluoro-n-propylsulfide and 6.09 g (80 mmol) of ammonium thiocyanate in 50 ml of acetic acid and 2.5 ml of water. The mixture was stirred for 5 hours and then left to stand overnight. The mixture was further heated and stirred for four hours at a temperature of from 70° to 80° C. Insoluble matters were removed by filtration while the mixture was still hot. The filtrate was poured into 200 ml of hot water, and the mixture was again subjected to hot filtration to remove insoluble matters. Under cooling with ice, 44 g of sodium carbonate was added to the filtrate, and the mixture was adjusted to pH6. Precipitated crystals were collected by filtration, then washed with water and dried to obtain 5.88 g (yield: 83.9%) of 2-amino-6-(heptafluoro-n-propylthio)benzoimidazole of the following structural formula (10) as slightly yellow crystals. MASS spectrum $M^+=350$, and the melting point was from 152° to 154° C. The IR spectrum is shown in FIG. 4.

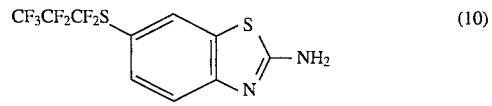
(10)

EXAMPLE 1

(a) Preparation

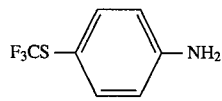

4.83 g of p-aminophenyltrifluoromethylsulfide of the above structural formula (1) and 7.61 g of ammonium thiocyanate were dissolved in a mixed solution of 62.5 ml of acetic acid and 3.1 ml of water, and a solution containing 5.0 g of bromine in 12.5 ml of acetic acid was dropwise added thereto at 10° C. The mixture was stirred for two hours and then left to stand overnight. The mixture was then heated to 70° C. and stirred for 4 hours. Then, the mixture was filtered while it was still hot, and the filtrate was poured into 250 ml of hot water. Precipitated crystals were filtered off. To the filtrate, sodium carbonate was added to bring the pH to 6, whereupon precipitated crystals were collected by filtration, washed with water and dried to obtain 5.21 g of a compound of the following structural formula (2) as slightly yellow crystals (MASS spectrum $M^+$=250).

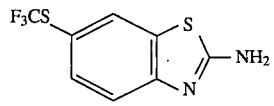

2.50 g of 2-amino-6-trifluoromethylthiobenzothiazole of the above structural formula (2) thus obtained, was dissolved in 17.8 g of phosphoric acid and 0.99 g of sulfuric acid, and 6.3 ml of acetic acid and 0.85 g of sodium nitrate were added thereto. Then, 2.43 g of sulfuric acid was added thereto at a temperature of from 0° to 5° C., and the solution was diazotized by means of 3.47 g of 44% nitrosyl sulfuric acid at a temperature of from 0° to −5° C. The diazotized solution thereby obtained, was dropwise added to a solution having 3.73 g of 2-dipropylaminoanisole-4-sulfonic acid, 0.4 g of urea and 4.0 g of sodium acetate dissolved in 150 ml of methanol, at a temperature of from 0° to 5° C., while maintaining the pH at: a level of from 4 to 6 by means of an alkali compound such as an aqueous ammonia. The mixture was stirred for two hours and then left to stand overnight. Precipitated crystals were collected by filtration and dried to obtain 4.92 g of a compound of the following structural formula (3) as dark brown crystals.

This compound had $\lambda_{max}$ (in methanol) of 561 nm.

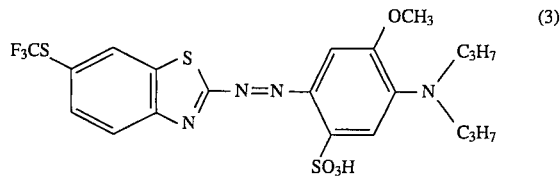

4.06 g of the azo compound of the structural formula (3) obtained as described above, was dissolved in 300 ml of methanol, and a solution containing 2.21 g of nickel acetate in 30 ml of methanol, was added thereto at a temperature of from 15 to 18° C. Then, the mixture was stirred at room temperature for 5 hours. Precipitated crystals were collected by filtration, washed with methanol and dried to obtain 2.66 g of a nickel chelate compound as dark brown crystals. This compound had $\lambda_{max}$ (in chloroform) of 688 nm ($\epsilon$=1.40×10$^5$) (see FIG. 1). Further, its melting point was higher than 250° C.

The infrared absorption spectrum of this compound is shown in FIG. 2.

(b) Recording medium 0.15 g of the nickel chelate compound of an azo compound obtained in the above preparation step (a) was dissolved in 7.5 g of octafluoropentanol and filtered through a filter of 0.22 μm to obtain a solution. 5 ml of this solution was dropped on an injection molded polycarbonate resin substrate (diameter: 5 inches) provided with a groove having a depth of 700 Å and a width of 0.7 μm and coated by a spinning method at a rotational speed of 500 rpm. After the coating, the coating layer was dried at 60° C. for 10 minutes. The maximum absorption wavelength of the coating layer was 713 nm.

FIG. 3 shows the absorption spectrum of the coating layer.

Then, on this coating layer, a film of gold was formed in a thickness of 2,000 Å by a sputtering method to form a reflective layer. Further, on this reflective layer, an ultraviolet-curable resin was spin-coated and cured by irradiation with ultraviolet rays to form a protective layer having a thickness of 10 μm.

(c) Optical recording

While rotating the above recording medium at a speed of 1.4 m/s, a semiconductor laser beam having a center wavelength of 780 nm was irradiated with a recording power of 6.6 mW to record EFM signals. Then, this recorded portion was reproduced by a CD player with a semiconductor laser having a center wavelength of 780 nm, whereby excellent reproduction signals were obtained.

Further, tests for light resistance (Xenone Fade Meter Accelerated Test; 60 hours) and storage stability (70° C., 85% RH; 500 hours) were conducted, whereby no deterioration in the sensitivity and reproduction signals was observed as compared with the initial values, and this medium was found to be excellent as an optical recording medium.

COMPARATIVE EXAMPLE 1

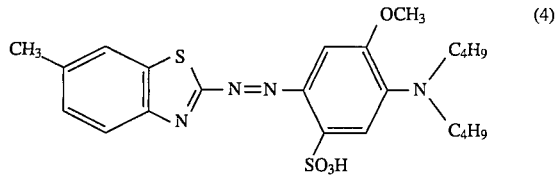

A nickel chelate compound prepared from an azo compound of the above structural formula (4) and nickel acetate, was coated in the same manner as in Example 1, and a reflective layer and a protective layer were formed in the same manner to obtain a disc, and the sensitivity and the reflectance were evaluated and compared, whereby the sensitivity was found to be inferior (sensitivity: 7.5 mW) as compared with the optical recording medium of Example 1 of the present invention.

EXAMPLE 2

(a) Preparation

The preparation was conducted in the same manner as in Example 1 except that 20.88 g of 4-(methylmercapto)aniline of the following structural formula (5):

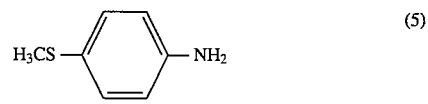

was used instead of p-aminotrifluoromethylsulfide used in Example 1, to obtain 11.72 g of a benzothiazole derivative of the following structural formula (6) (MASS spectrum $M^+=196$).

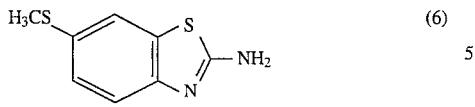

In the same manner as in Example 1 except that 1.96 g of 2-amino-6-methylthiobenzothiazole of this structural formula (6) was used, 1.94 g of crystals of an azo compound of the following structural formula (7) were obtained. This compound had $\lambda_{max}$ (in methanol) of 561 nm.

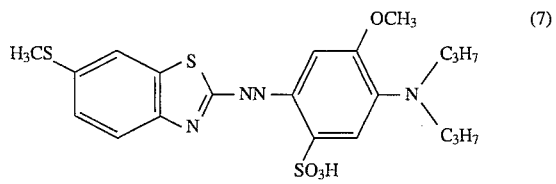

In the same manner as in Example 1 except that 1.48 g of the azo compound of this structural formula (7) was used, 1.06 g of dark brown crystals of a nickel chelate compound were obtained. The absorption spectrum of this compound in a chloroform solution had $\lambda_{max}$ of 690 nm ($\epsilon=1.34\times10^5$) (see FIG. 4). Further, its melting point was higher than 250° C.

Figure 5:
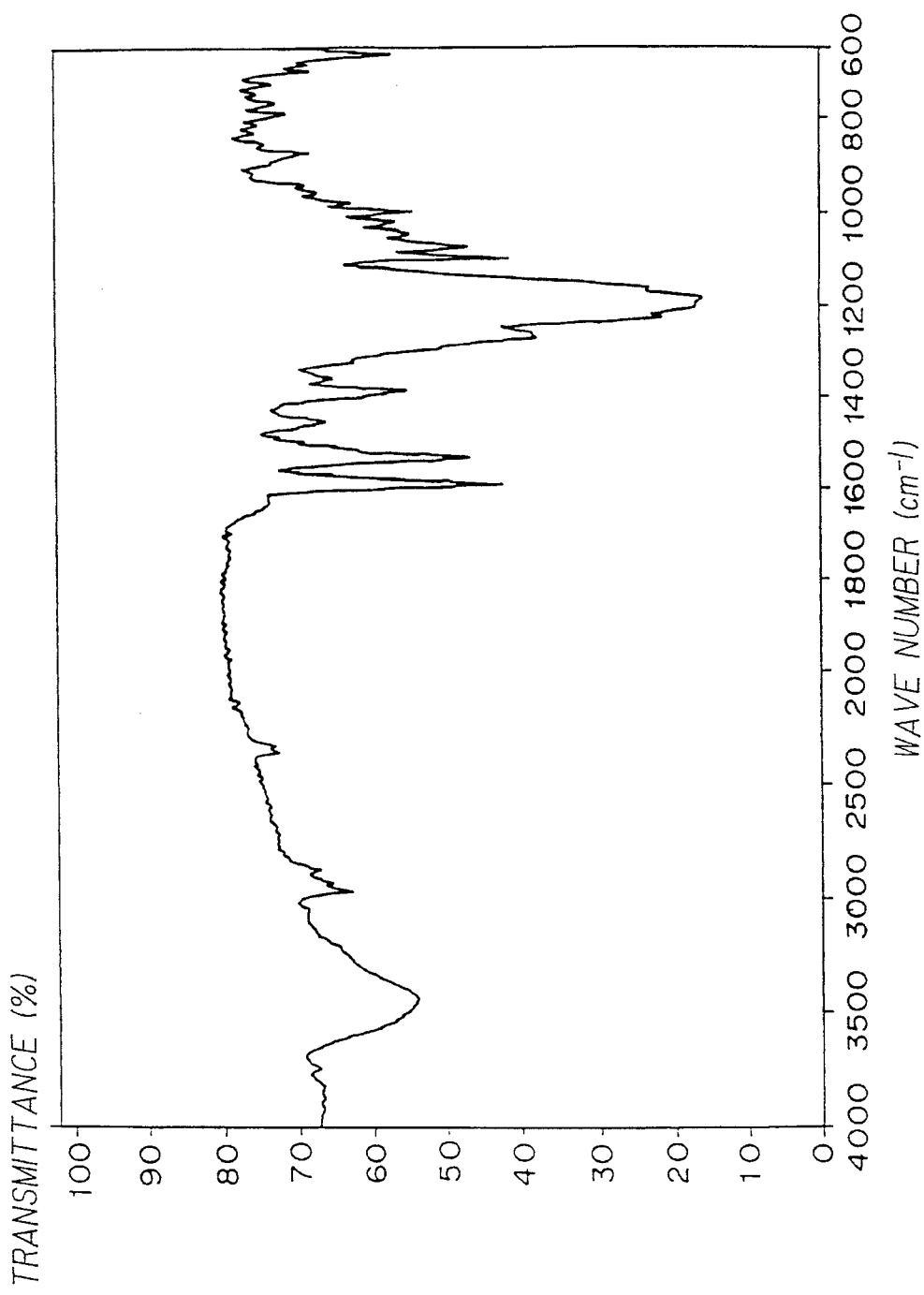
FIG. 5 is a graph showing an infrared absorption spectrum of the nickel chelate compound of Example 2.

The infrared absorption spectrum of this compound is shown in FIG. 5.

(b) Recording medium 0.15 g of the nickel chelate compound of an azo compound obtained in the above preparation step (a) was dissolved in 7.5 g of octafluoropentanol and filtered through a filter of 0.22 μm to obtain a solution. 5 ml of this solution was dropped on an injection-molded polycarbonate resin substrate (diameter: 5 inches) provided with a groove having a depth of 700 Å and a width of 0.7 μm and coated by a spin coating method at a rotational speed of 500 rpm. After the coating, the coating layer was dried at 60° C. for 10 minutes. The maximum absorption wavelength of the coating layer was 717 nm.

Figure 6:
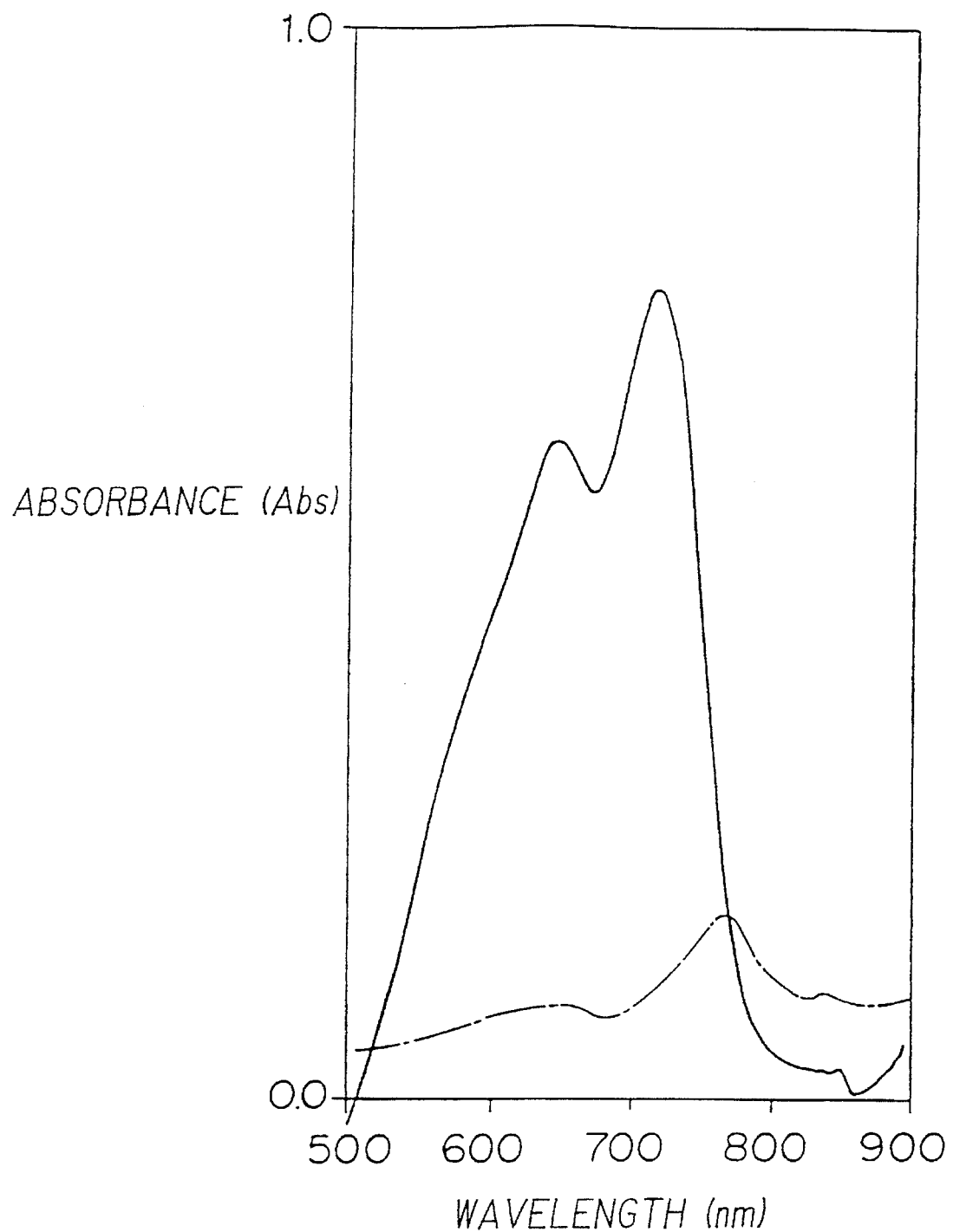
FIG. 6 is a graph showing a visible range absorption spectrum of a thin coating film of the nickel chelate compound of Example 2.

FIG. 6 shows the absorption spectrum of the coating layer.

Then, on this coating layer, a film of gold was formed in a thickness of 2,000 Å by a sputtering method to form a reflective layer. Further, on this reflective layer, an ultraviolet-curable resin was spin-coated and then cured by irradiation with ultraviolet rays to form a protective layer having a thickness of 10 μm.

(c) Optical recording

While rotating the above recording medium at a speed of 1.4 m/s, a semiconductor laser beam having a center wavelength of 780 nm was irradiated with a recording power of 6.9 mW to record EFM signals. Then, this recorded portion was reproduced by a CD player with a semiconductor laser having a center wavelength of 780 nm, whereby excellent reproduction signals were obtained.

Further, tests for light resistance (Xenone Fade Meter Accelerated Test; 60 hours) and storage stability (70° C., 85% RH; 500 hours) were conducted, whereby no deterioration in the sensitivity and reproduction signals was observed as compared with the initial values, and this medium was found to be excellent as an optical recording medium.

EXAMPLE 3

(a) Preparation 24.3 g of 4-aminophenylpentafluoroethylsulfide of the following structural formula (8):

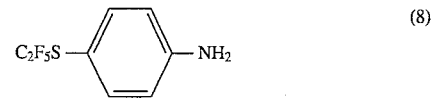

and 30.5 g of ammonium thiocyanate were dissolved in 240 ml of acetic acid and 13 ml of water, and a solution containing 20.0 g of bromine in 50 ml of acetic acid, was dropwise added thereto at 10° C. The mixture was stirred for 4 hours, then heated to 70° C. and stirred for 3 hours. The mixture was filtered while it was still hot. The filtrate was poured into 900 ml of hot water. Precipitated crystals were removed by filtration. To the filtrate, 174 g of sodium carbonate was added to adjust the pH to 5, whereupon precipitated crystals were collected by filtration, washed with water and dried to obtain 22.0 g (yield: 73.3%) of a compound of the following structural formula (9) as slightly yellow crystals. MASS spectrum $M^+=243$

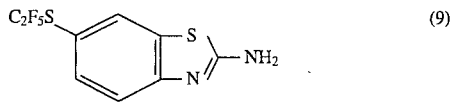

A solution containing 15.0 g of 2-amino-6-(pentafluoroethylthio)benzothiazole of the formula (9) in 63.0 ml of acetic acid and 63.0 ml of propionic acid, was added to 89.0 g of phosphoric acid and 4.95 g of sulfuric acid. 4.25 g of sodium nitrate was added thereto, and then 12.2 g of sulfuric acid was dropwise added thereto at a temperature of from 0° to 5° C. Further, 17.4 g of 44% nitrosyl sulfuric acid was dropwise added thereto at a temperature of from 0° to −5° C., and then the mixture was stirred for one hour for diazotization. The obtained diazotized solution was dropwise added to a solution having 18.7 g of 2-di(n-propyl)aminoanisole-4-sulfonic acid, 2.0 g of urea and 20.0 g of sodium acetate dissolved in 750 ml of methanol, at a temperature of from 0° to 5° C. while maintaining the pH at a level of from 4 to 6 by means of an alkali compound such as aqueous ammonia. The mixture was stirred for two hours and then left to stand overnight. Precipitated crystals were collected by filtration, suspended and washed with water and toluene and dried to obtain 20.3 g (yield: 67.9%) of a compound of the following structural formula (10) as dark brown crystals. This compound had $\lambda_{max}$ (in methanol) of 562 nm. MASS spectrum $M^+=598$

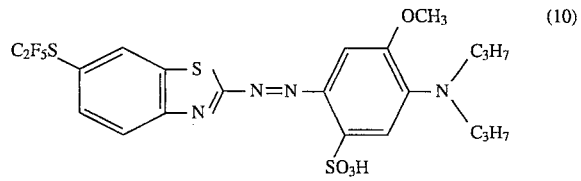

Figure 7:
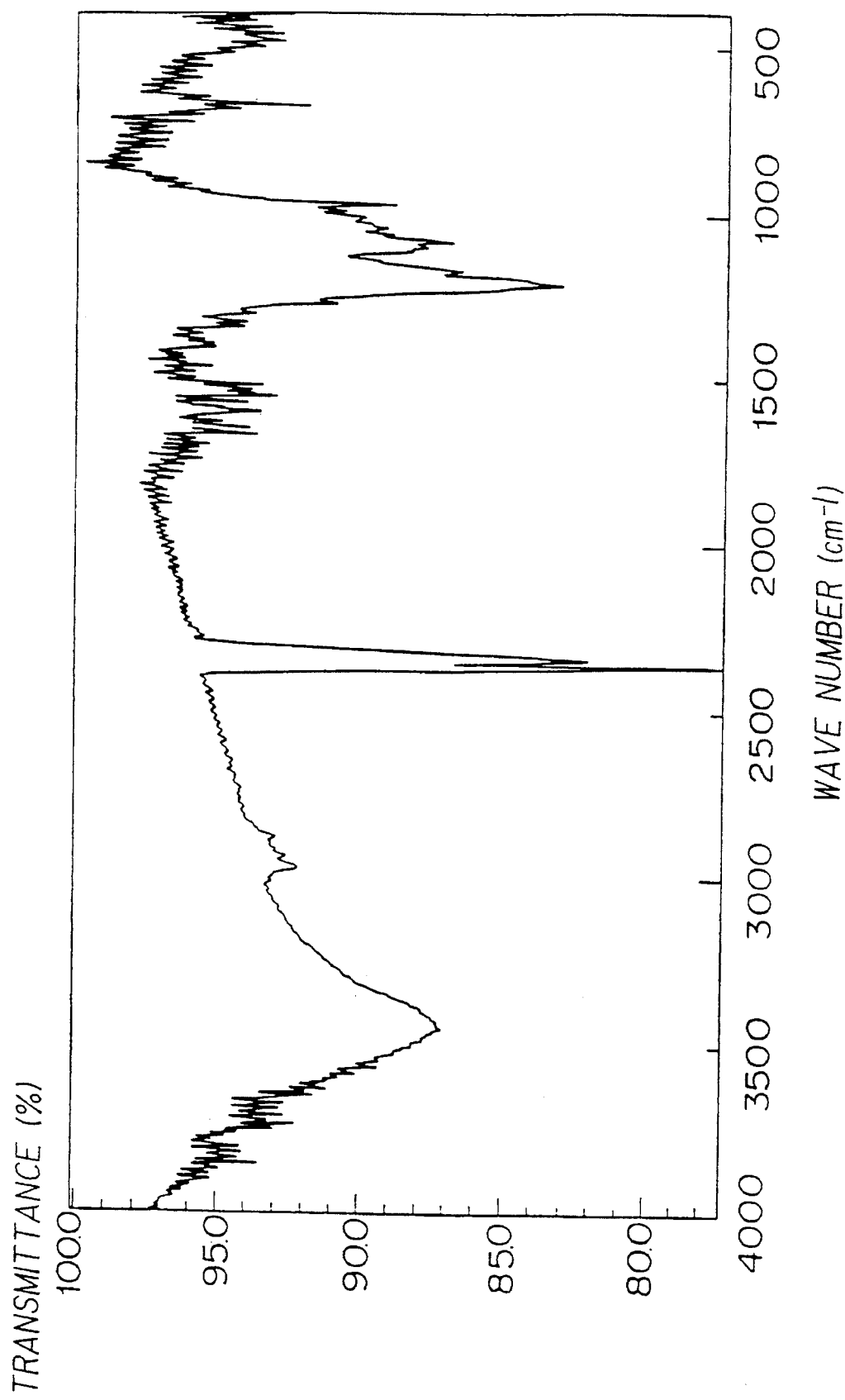
FIG. 7 is a graph showing an infrared absorption spectrum of the nickel chelate compound of Example 3 of the present invention.
Figure 8:
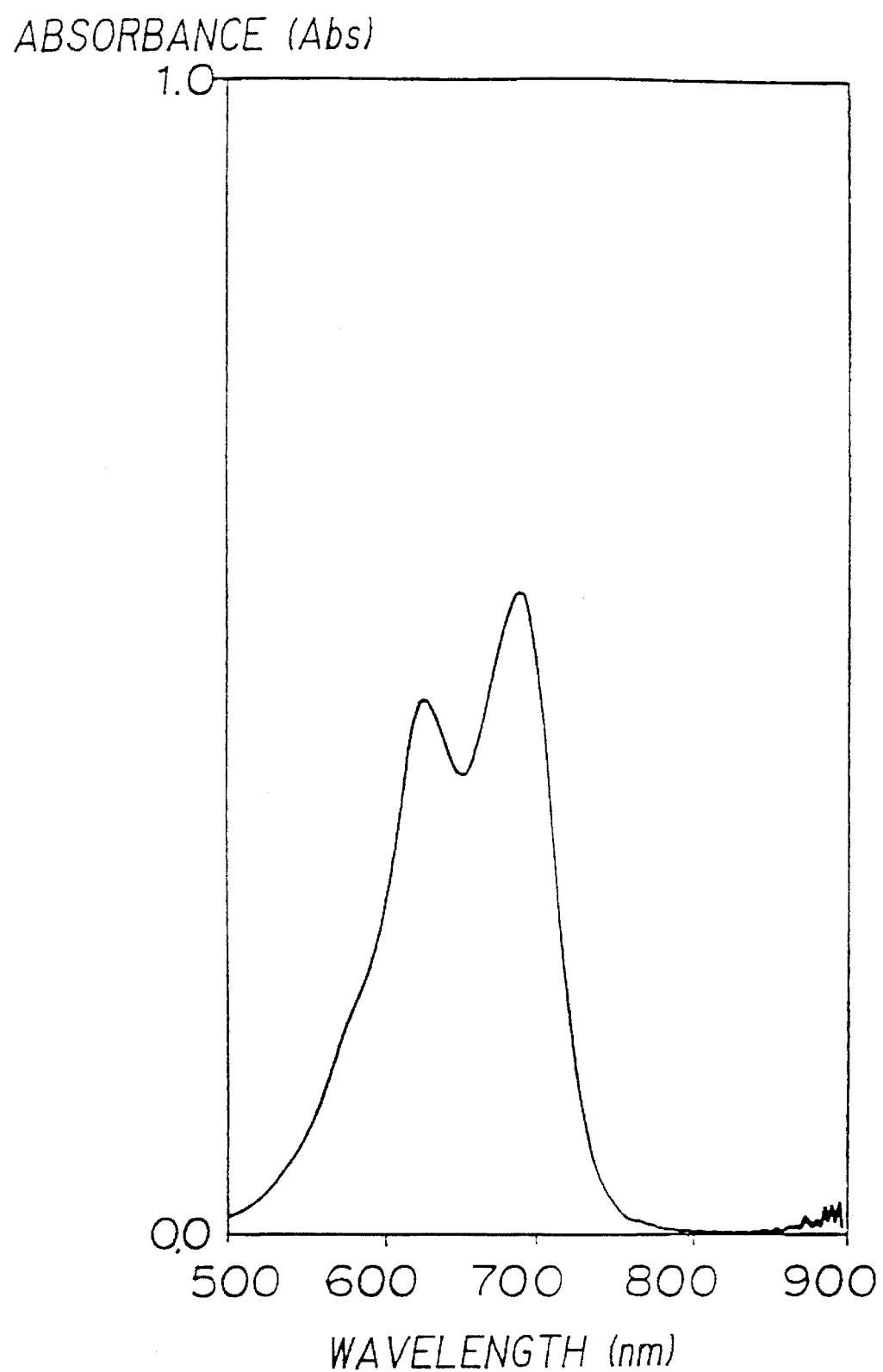
FIG. 8 is a graph showing a visible range absorption spectrum of the nickel chelate compound of Example 3 of the present invention as measured in a chloroform solution, wherein the ordinate represents absorbance, and the abscissa represents wavelength (nm).

19.5 g of the azo compound of the formula (10) as described above, was dissolved in 1,200 ml of methanol, and a solution containing 9.73 g of nickel acetate in 140 ml of methanol, was added thereto at a temperature of from 20° to 22° C. Then, the mixture was stirred for 7 hours. Precipitated crystals were collected by filtration, washed with methanol and dried to obtain 15.2 g of a nickel complex as dark brown crystals. This product had $\lambda_{max}$ (in chloroform) of 690 nm. Melting point >250° C., MASS spectrum $MH^+=1,253$ Further, the infrared absorption spectrum of this product are shown in FIG. 7, and the visible absorption spectrum is shown in FIG. 8.

(b) Recording medium 0.21 g of the nickel complex of an azo compound prepared in the above preparation step (a) was dissolved in 7.5 g of octafluoropentanol and filtered through a filter of 0.22 μm to obtain a solution. 5 ml of this solution was dropped on an injection molded polycarbonate resin substrate (5 inches) provided with a groove having a depth of 700 Å and a width of 0.7 μm and coated by a spinning method at a rotational speed of 500 rpm. After the coating, the coating layer was dried at 60° C. for 10 minutes. The maximum absorption wavelength of the coating layer was 709 nm.

Figure 9:
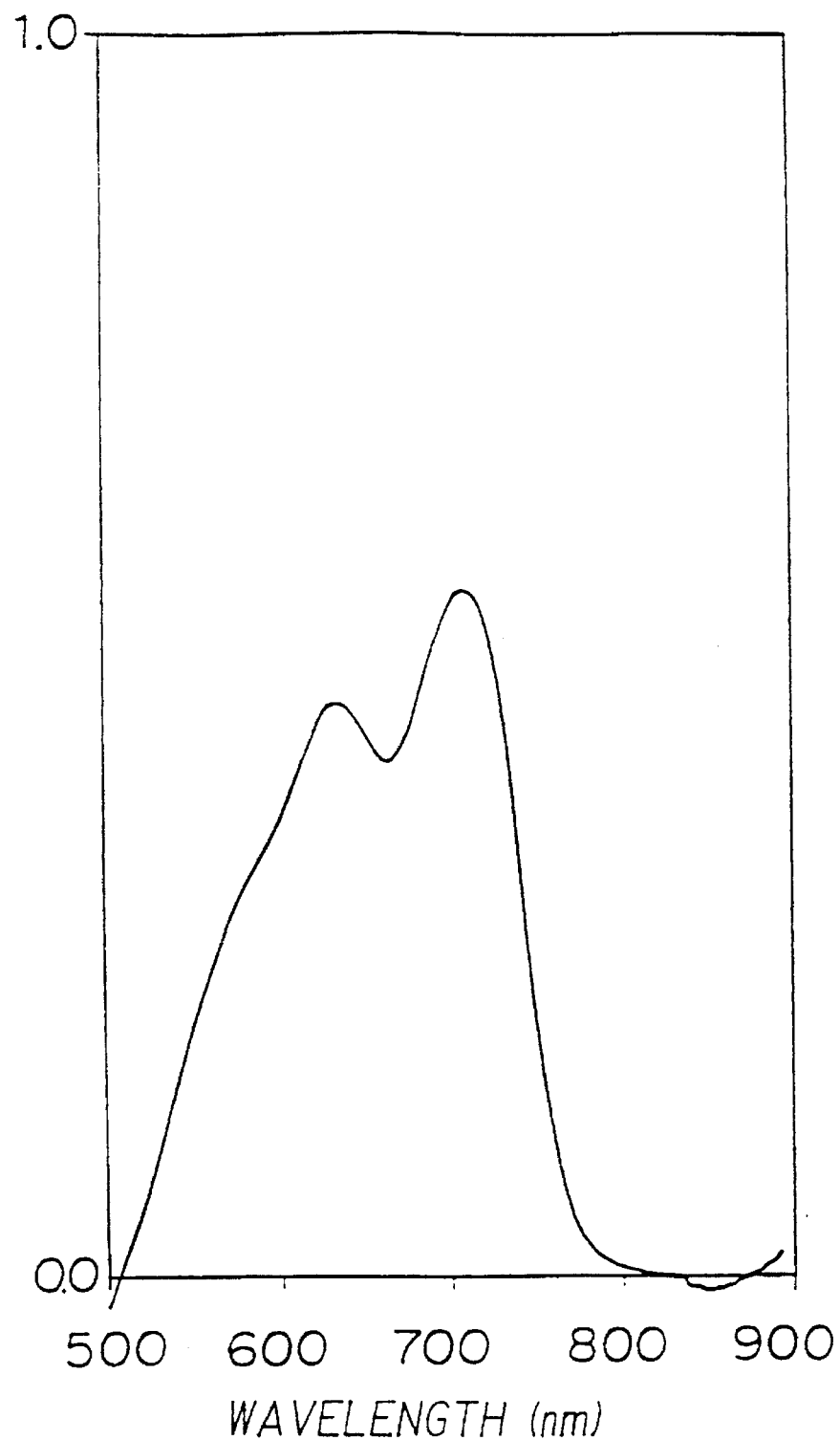
FIG. 9 is a graph showing a visible range absorption spectrum of the thin coating film of the nickel chelate compound of Example 3 of the present invention, wherein the ordinate represents absorbance, and the abscissa represents wavelength (nm).

FIG. 9 shows the absorption spectrum of the coating layer.

Then, on this coating layer, a film of gold was formed in a thickness of 2,000 Å by a sputtering method to form a reflective layer. Further, on this reflective layer, an ultraviolet-curable resin was spin-coated and then cured by irradiation with ultraviolet rays to form a protective layer having a thickness of 10 μm.

(c) Optical recording

While rotating the above recording medium at a speed of 1.4 m/s, a semiconductor laser beam having a center wavelength of 780 nm was irradiated with a recording power of 6.8 mW to record EFM signals. Then, this recorded portion was reproduced by a CD player with a semiconductor laser having a center wavelength of 780 nm, whereby excellent reproduction signals were obtained.

Further, tests for light resistance (Xenone Fade Meter Accelerated Test; 60 hours) and storage stability (70° C., 85% RH; 500 hours) were conducted, whereby no deterioration in the sensitivity and reproduction signals was observed as compared with the initial values, and this medium was found to be excellent as an optical recording medium.

EXAMPLE 4

(a) Preparation

A solution containing 2.1 g of 2-amino-6-(pentafluoroethylthio)benzothiazole of the formula (9) in 8.8 ml of acetic acid and 8.8 ml of propionic acid, was added to 12.5 g of phosphoric acid and 0.69 g of sulfuric acid. 0.60 g of sodium nitrate was added thereto, and then 1.70 g of sulfuric acid was dropwise added thereto at a temperature of from 0° to 5° C. Further, 2.49 g of 44% nitrosyl sulfuric acid was dropwise added thereto at a temperature of from 0° to −5° C., and then the mixture was stirred for one hour for diazotization. The diazotized solution thus obtained, was dropwise added to a solution having 3.0 g of 2-di(n-butyl)aminophenetol-4-sulfonic acid, 0.28 g of urea and 2.8 g of sodium acetate dissolved in 105 ml of methanol, at a temperature of from 0° to 5° C., while maintaining the pH at a level of from 4 to 6 by means of an alkali compound such as aqueous ammonia. The mixture was stirred for 3 hours and then left to stand overnight. Precipitated crystals were collected by filtration, suspended and washed with water and toluene and dried to obtain 3.19 g of a compound of the following structural formula (11) as dark brown crystals (yield: 71.1.%). Further, this compound had $\lambda_{max}$ (in methanol) of 568 nm.

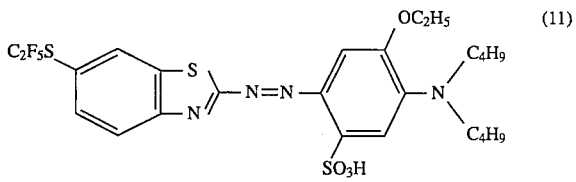

3.0 g of the azo compound of the formula (11) obtained as described above, was dissolved in 300 ml of methanol, and a solution containing 1.40 g of nickel acetate in 20 ml of methanol, was added thereto at a temperature of from 20° to 22° C. Then, the mixture was stirred for 5 hours. Precipitated crystals were collected by filtration, washed with methanol and dried to obtain 1.96 g of a nickel complex as dark brown crystals. This product had $\lambda_{max}$ (in chloroform) of 691 nm. Melting point >250° C.

Figure 10:
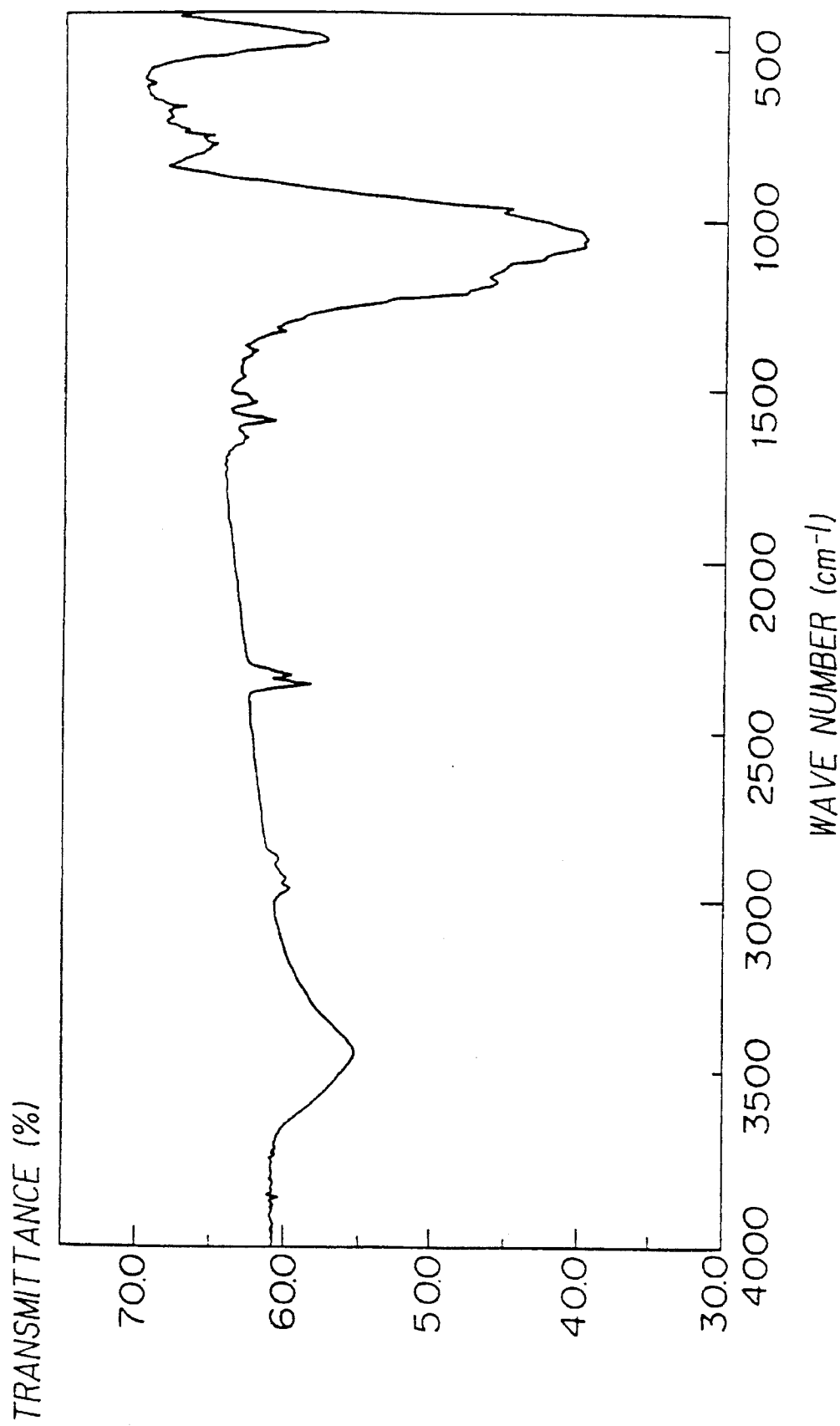
FIG. 10 is a graph showing an infrared absorption spectrum of the nickel chelate compound of Example 4 of the present invention.
Figure 11:
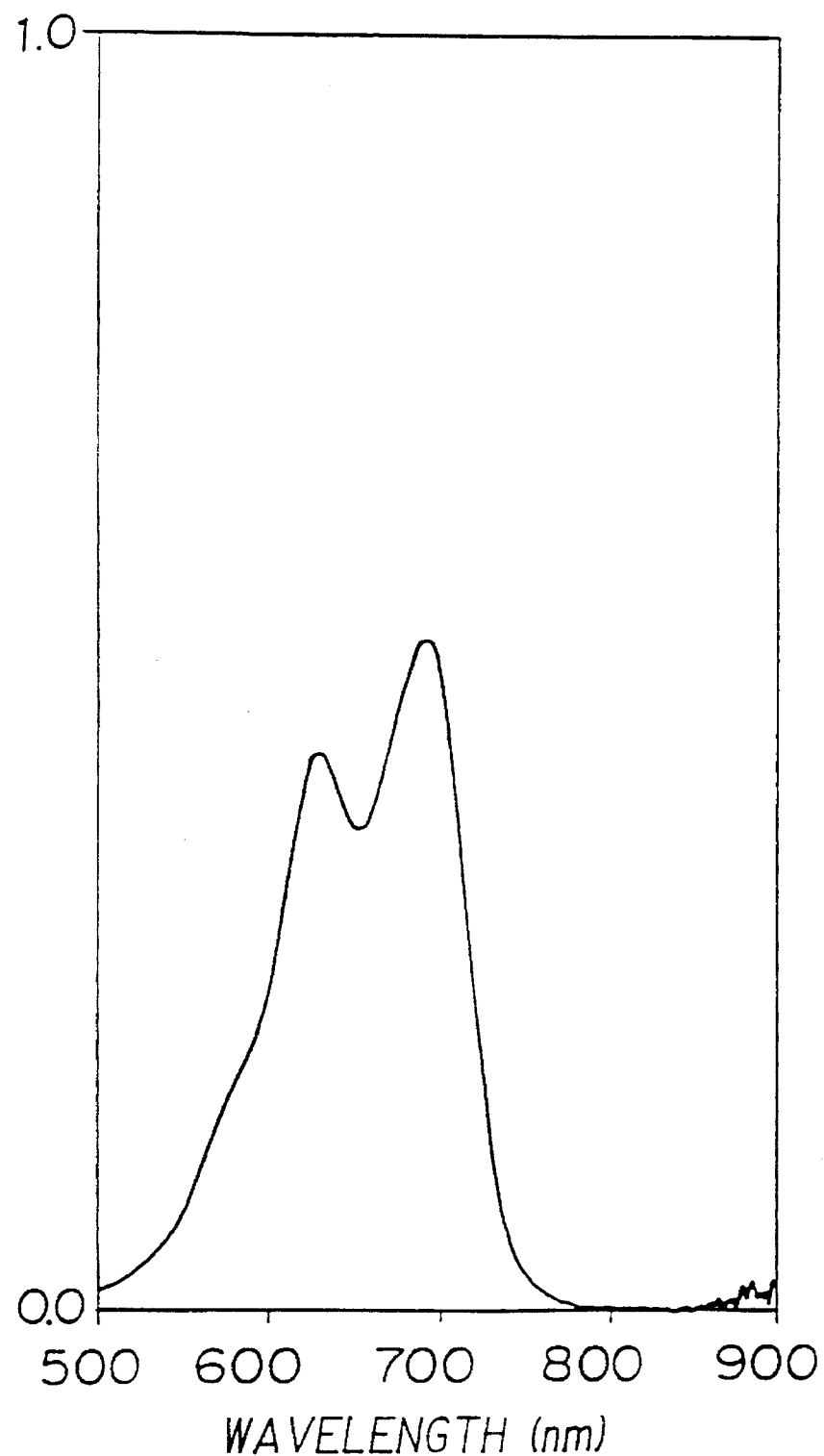
FIG. 11 is a graph showing a visible range absorption spectrum of the nickel chelate compound of Example 4 of the present invention as measured in a chloroform solution, wherein the ordinate represents absorbance, and the abscissa represents wavelength (nm).

Further, the infrared absorption spectrum of this product is shown in FIG. 10, and the visible absorption spectrum is shown in FIG. 11.

(b) Recording medium 0.12 g of the nickel complex of an azo compound obtained in the above preparation step (a) was dissolved in 7.5 g of octafluoropentanol and filtered through a filter of 0.22 μm to obtain a solution. 5 ml of this solution was dropped on an injection molded polycarbonate resin substrate (5 inches) provided with a groove having a depth of 700 Å and a width of 0.7 μm and coated by a spinning method at a rotational speed of 500 rpm. After the coating, the coating layer was dried at 60° C. for 10 minutes. The maximum absorption wavelength of the coating layer was 708 nm.

Figure 12:
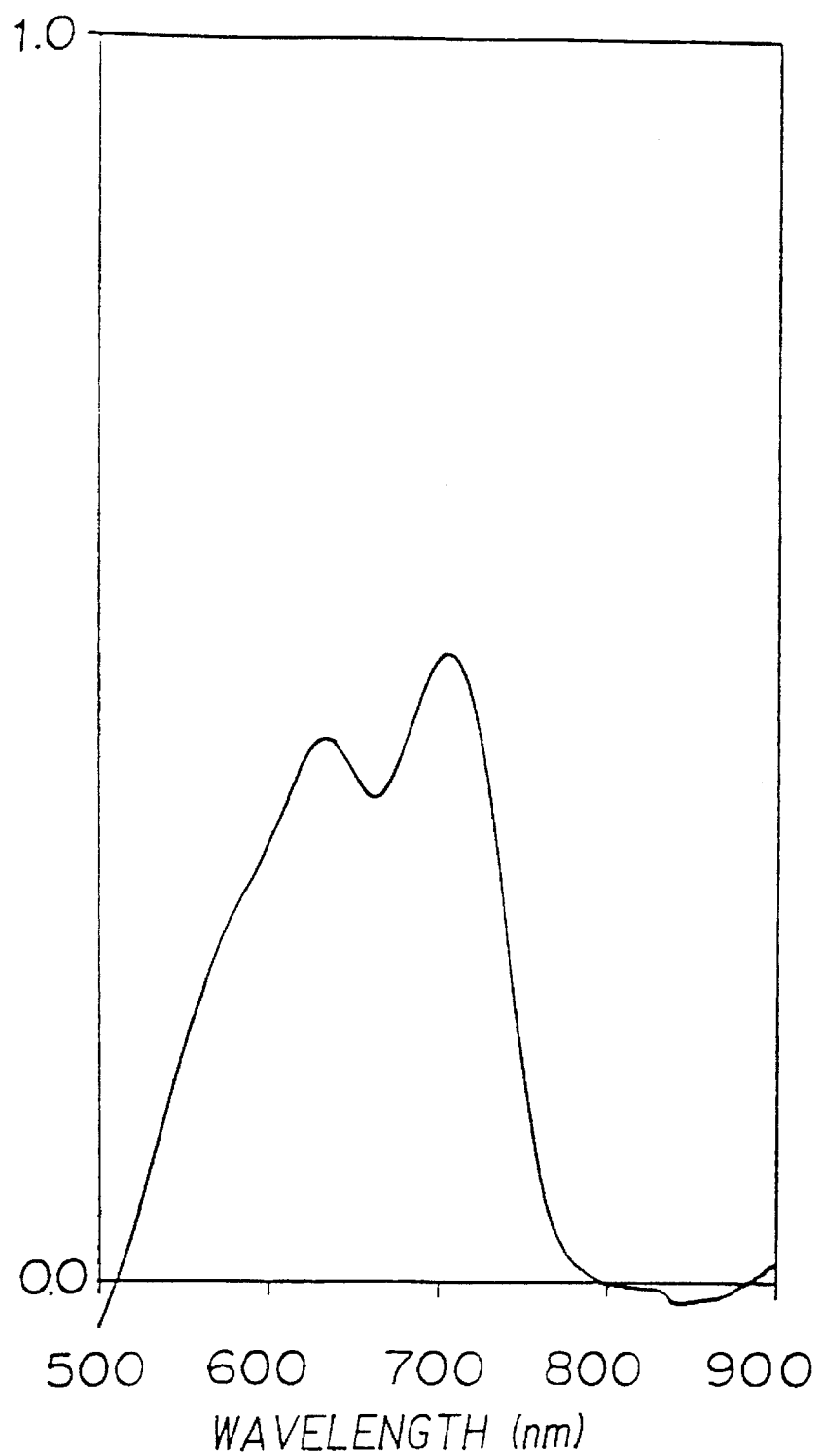
FIG. 12 is a graph showing a visible range absorption spectrum of the thin coating film of the nickel chelate compound of Example 4 of the present invention, wherein the ordinate represents absorbance, and the abscissa represents wavelength (nm).

FIG. 12 shows the absorption spectrum of the coating layer.

Then, on this coating layer, a film of gold was formed in a thickness of 2,000 Å by a sputtering method to form a reflective layer. Further, on this reflective layer, an ultraviolet-curable resin was spin-coated and then cured by irradiation with ultraviolet rays to form a protective layer having a thickness of 10 μm.

(c) Optical recording

While rotating the above recording medium at a speed of 1.4 m/s, a semiconductor-laser beam having a center wavelength of 780 nm was irradiated with a recording power of 6.8 mW to record EFM signals. Then, this recorded portion was reproduced by a CD player with a semiconductor laser having a center wavelength of 780 nm, whereby excellent reproduction signals were obtained.

Further, tests for light resistance (Xenone Fade Meter Accelerated Test; 60 hours) and storage stability (70° C., 85% RH; 500 hours) were conducted, whereby no deterioration in the sensitivity and reproduction signals was observed as compared with the initial values, and this medium was found to be excellent as an optical recording medium.

EXAMPLE 5

A solution obtained by using a compound as identified in Table 1 instead of the compound used in Example 1, was coated on a substrate, to obtain an optical recording medium having a coating layer with the maximum absorption wavelength as identified in Table 1. To the recording medium thus obtained, recording was conducted by means of a semiconductor laser as a light source, whereby the recording sensitivity was good, and the light resistance and storage stability were excellent.

TABLE 1

| Azo compound | Metal compound | $\lambda_{max}$ in solution | $\lambda_{max}$ of coating layer |
| --- | --- | --- | --- |
| $C_2F_5S$-benzothiazole-N=N-phenyl($OC_2H_5$, $N(C_3H_7)_2$, $SO_3H$) | $Ni(CH_3COO)_2 \cdot 4H_2O$ | 692 nm | 708 |
| $C_2F_5S$-benzothiazole-N=N-phenyl($OCH_3$, $N(C_4H_9)_2$, $SO_3H$) | $Ni(CH_3COO)_2 \cdot 4H_2O$ | 691 nm | 709 nm |
| $C_2F_5S$-benzothiazole-N=N-phenyl($OCH_3$, $N(C_4H_9)_2$, $SO_3H$) | $Ni(CH_3COO)_2 \cdot 4H_2O$ | 688 nm | 709 nm |
| $C_2F_5S$-benzothiazole-N=N-phenyl($OCH_3$, $N(C_3H_7)_2$, $SO_3H$) | $Ni(CH_3COO)_2 \cdot 4H_2O$ | 691 nm | 707 nm |
| $C_3F_7S$-benzothiazole-N=N-phenyl($OCH_3$, $N(C_3H_7)_2$, $SO_3H$) | $Ni(CH_3COO)_2 \cdot 4H_2O$ | 688 nm | 709 nm |
| $C_4F_9S$-benzothiazole-N=N-phenyl($OCH_3$, $N(C_3H_7)_2$, $SO_3H$) | $Ni(CH_3COO)_2 \cdot 4H_2O$ | 688 nm | 706 nm |
| $CF_3CH_2S$-benzothiazole-N=N-phenyl($OCH_3$, $N(C_3H_7)_2$, $SO_3H$) | $Ni(CH_3COO)_2 \cdot 4H_2O$ | 695 nm | 727 nm |
| $CH_3S$-benzothiazole-N=N-phenyl($OC_2H_5$, $N(C_3H_7)_2$, $SO_3H$) | $Ni(CH_3COO)_2 \cdot 4H_2O$ | 693 nm | 717 nm |

The metal chelate compound of an azo compound of the present invention has a high level of solubility to an organic solvent, so that it can be applied by coating in the form of a coating solution, and yet it has good sensitivity and excellent light resistance and storage stability. Therefore, an optical recording medium employing such a metal chelate compound is very useful from the industrial viewpoint.

What is claimed is:

1. An azo metal chelate compound of an azo compound and a metal, wherein the azo compound is a compound of the following formula (V):

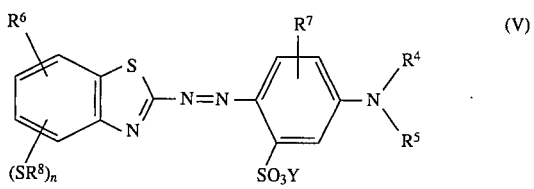

wherein each of $R^4$ and $R^5$, independent of each other, is a $C_{1-6}$ alkyl group or a $C_{2-7}$ alkoxyalkyl group, each of $R^6$ and $R^7$ which are independent of each other, is a hydrogen atom, a $C_{1-6}$ alkyl group, a $C_{1-6}$ alkoxy group or a halogen atom, $R^8$ is a $C_{1-6}$ alkyl group which is substituted by at least one fluorine atom, Y is a hydrogen atom or a cation, and n is an integer of from 1 to 3.

2. The azo metal chelate compound of claim 1, wherein said metal is Ni, Co, Fe, Ru, Rh, Pd, Os, Ir or Pt.

3. The azo metal chelate compound of claim 1, wherein Y is a hydrogen atom.

4. The azo metal chelate compound of claim 3, wherein said metal is Ni, Co, Fe, Ru, Rh, Pd, Os, Ir or Pt.

* * * * *